United States Patent
Waku et al.

(10) Patent No.: US 10,563,167 B2
(45) Date of Patent: *Feb. 18, 2020

(54) MICROORGANISM CULTURE SHEET

(75) Inventors: Shin-ichi Waku, Tokyo (JP); Michiko Miyagi, Tokyo (JP); Rui Saito, Tokyo (JP); Tetsuji Ueki, Tokyo (JP); Takuma Baba, Tokyo (JP); Mai Kinoshita, Tokyo (JP)

(73) Assignee: Dai Nippon Printing Co., Ltd., Tokyo (JP)

(*) Notice: Subject to any disclaimer, the term of this patent is extended or adjusted under 35 U.S.C. 154(b) by 293 days.

This patent is subject to a terminal disclaimer.

(21) Appl. No.: 13/575,906

(22) PCT Filed: Jan. 26, 2011

(86) PCT No.: PCT/JP2011/051502
§ 371 (c)(1),
(2), (4) Date: Nov. 9, 2012

(87) PCT Pub. No.: WO2011/093342
PCT Pub. Date: Aug. 4, 2011

(65) Prior Publication Data
US 2013/0084624 A1  Apr. 4, 2013

(30) Foreign Application Priority Data
Jan. 29, 2010  (JP) .................................. 2010-019012

(51) Int. Cl.
*C12N 1/20* (2006.01)
*C12Q 1/04* (2006.01)
(Continued)

(52) U.S. Cl.
CPC ................ *C12N 1/20* (2013.01); *C12M 1/16* (2013.01); *C12Q 1/02* (2013.01); *C12Q 1/04* (2013.01);
(Continued)

(58) Field of Classification Search
CPC . C12Q 1/04; C12Q 1/24; C12Q 1/045; C12Q 1/02; C12M 1/16; C12M 1/22;
(Continued)

(56) References Cited

U.S. PATENT DOCUMENTS 3,827,942 A * 8/1974 Janik ..................... C12N 1/00
435/253.6
4,945,061 A 7/1990 Iskander
(Continued)

FOREIGN PATENT DOCUMENTS

CA  924224 A * 4/1973
EP  1179586   2/2002
(Continued)

OTHER PUBLICATIONS

Extended Search Report issued by Europoean Patent Office dated Dec. 13, 2013, in connection with related European Patent Application No. 11737055.1.

(Continued)

*Primary Examiner* — Allison M Fox
*Assistant Examiner* — Qing Xu
(74) *Attorney, Agent, or Firm* — Hamre, Schumann, Mueller & Larson, P.C.

(57) ABSTRACT

Provided is a microorganism culture sheet having an excellent efficiency for collection of environmental microorganisms and a method for measuring the environmental microorganisms with an excellent collection efficiency. Provided is a microorganism culture sheet including a base sheet, a dry culture layer formed on the base sheet, and a cover sheet covering the dry culture layer, wherein an adhesive layer and a release film are laminated on the inner surface of the cover sheet. Because the environmental microorganisms are collected using the adhesive layer, an excellent collection efficiency is provided.

11 Claims, 11 Drawing Sheets

Figure 1:
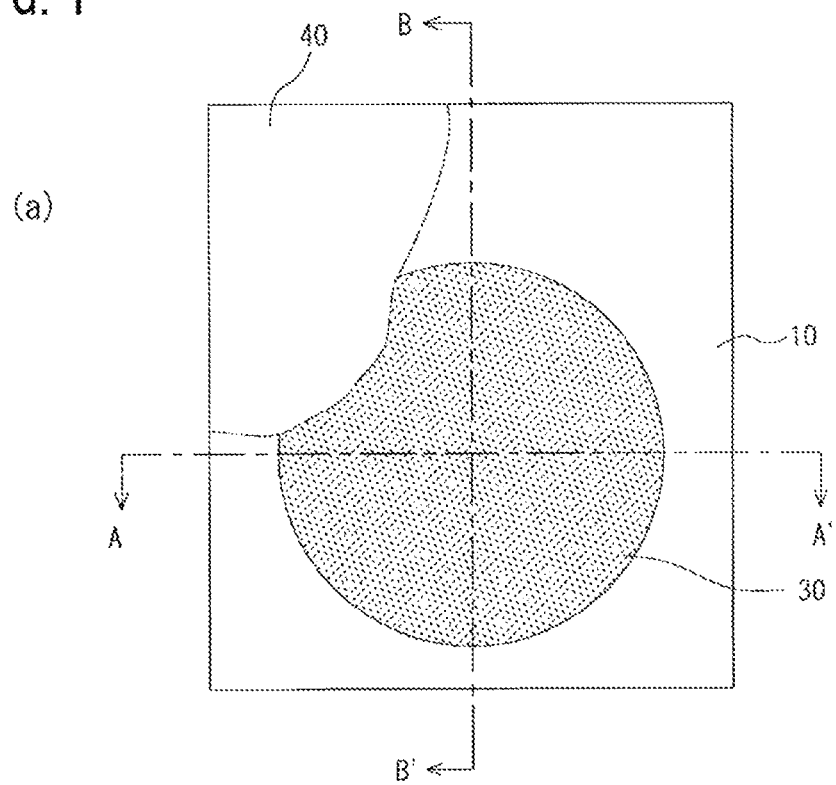
Figure 1:
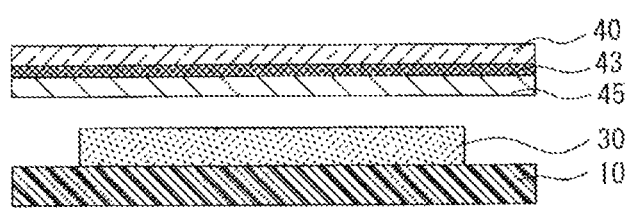
Figure 1:
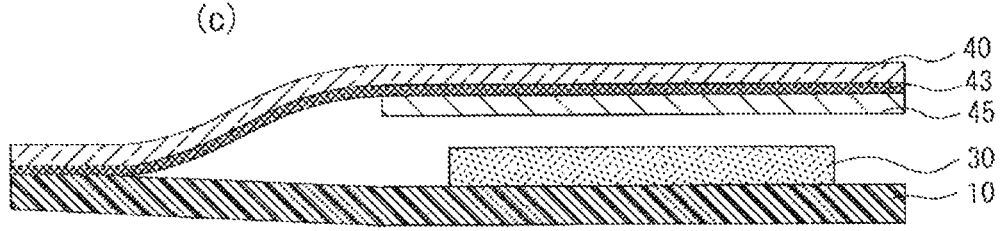

(51) Int. Cl.
  *C12Q 1/02* (2006.01)
  *C12M 1/16* (2006.01)
  *C12Q 1/24* (2006.01)
  *C12M 1/14* (2006.01)
  *C12M 1/00* (2006.01)
(52) U.S. Cl.
  CPC .............. *C12Q 1/24* (2013.01); *C12M 1/14* (2013.01); *C12M 23/22* (2013.01)
(58) Field of Classification Search
  CPC .......... C12M 1/26; C12M 1/30; C12M 25/06; C12M 25/14
  See application file for complete search history.

(56) References Cited

U.S. PATENT DOCUMENTS

| | | | |
|---|---|---|---|
| 5,622,761 A | | 4/1997 | Cole |
| 6,638,755 B1 * | | 10/2003 | Mizuochi et al. ......... 435/253.6 |
| 6,649,406 B1 * | | 11/2003 | Williams ................ C12Q 1/24 435/287.9 |
| 2005/0239200 A1 | | 10/2005 | Beckwith |
| 2010/0159597 A1 | | 6/2010 | Kuroda et al. |

FOREIGN PATENT DOCUMENTS

| | | | | |
|---|---|---|---|---|
| EP | 1743975 | | | 1/2007 |
| EP | 2455447 | A1 | | 5/2012 |
| JP | H0249705 | | | 10/1990 |
| JP | 08-280377 | | | 10/1996 |
| JP | 08-280377 | A | * | 10/1996 |
| JP | H0919282 | | | 1/1997 |
| JP | 09-075063 | | | 3/1997 |
| JP | H0975063 | | | 3/1997 |
| JP | 09-206062 | | | 8/1997 |
| JP | 2000-304663 | | | 11/2000 |
| JP | 2001-333796 | | | 4/2001 |
| JP | 2002171964 | A | | 6/2002 |
| JP | 2004515236 | | | 5/2004 |
| JP | 2006-230315 | | | 7/2006 |
| JP | 2006-230315 | | * | 9/2006 |
| JP | 2006230220 | A | * | 9/2006 |
| JP | 2006230315 | A | * | 9/2006 |
| JP | 2008-101971 | | | 1/2008 |
| JP | 2008-193919 | | | 8/2008 |
| JP | 2008-193919 | A | * | 8/2008 |
| JP | 2008193919 | A | * | 8/2008 |
| JP | 2008-278772 | | | 11/2008 |
| JP | 2009-153500 | A | * | 7/2009 |
| JP | 2009153501 | | | 7/2009 |
| JP | 2009207394 | A | | 9/2009 |
| JP | 2009207394 | A | * | 9/2009 |
| WO | 8202563 | | | 8/1982 |
| WO | 96/38533 | A1 | | 12/1995 |
| WO | 0144437 | | | 6/2001 |
| WO | 01/38559 | A2 | | 5/2005 |
| WO | 2008153063 | | | 12/2008 |

OTHER PUBLICATIONS

Wikipedia, https://en.wikipedia.org/wiki/Petri_dish, archived Dec. 17, 2008, accessed Jun. 19, 2019 (2 pages).
Steane, http://web.archive.org/web/20060424082858/http://www.biotopics.co.uk/microbes/tech.html, archived Apr. 24, 2006, accessed Dec. 5, 2016 (10 pages).
http://www.dictionary.com/browse/fixed, accessed Mar. 22, 2016 (9 pages).
U.S. Appl. No. 13/383,669, filed Jan. 12, 2012, US 2012-0107913 A1.

* cited by examiner (a)

(b)

(c)

(a)

(b)

(c)

MICROORGANISM CULTURE SHEET

PRIORITY CLAIM

This is a U.S. national stage of application No. PCT/JP2011/051502, filed on Jan. 26, 2011. Priority is claimed on the following application: Country: Japan, Application No.: 2010-019012, Filed: Jan. 29, 2010, the content of which is incorporated here by reference.

BACKGROUND OF THE INVENTION

1. Field of the Invention

The present invention relates to a microorganism culture sheet capable of collecting microorganisms on a solid surface of object or airborne microorganisms by an adhesive layer of a cover sheet with an excellent collection efficiency, a microorganism culture kit comprising the above-mentioned microorganism culture sheet and a gelling solution for a dry culture layer, and the like.

2. Description of the Related Art

As a method for checking if microorganisms are present or a method for measuring the number of the microorganisms, an agar pour plate method has been around and an agar medium formed in a Petri dish which is sterilized in advance is used. Also, for the purpose of hygiene control of production facilities for food products or pharmaceutical products, a stamp method has been known as a method for detecting bacteria attached to the surface of kitchen utensils and containers. This stamp method is a method in which an agar medium or the like is directly attached to a test object for detection of bacteria present on the surface thereof. A stamp medium obtained by solidifying an aqueous solution containing nutrients enabling bacterial proliferation into a stamp-like shape is used such that the collected bacteria can be cultured directly after the collection. In consideration of the stamp medium being pushing against an object to be inspected, one in which a Petri dish body filled with the agar medium or the like is assembled with a removable lid is used. These Petri dish body and lid are both made up of a plastic such as polypropylene or the like molded article. The Petri dish body has a configuration where a protruded circular recess is formed on a square-shape or round-shape base. The lid has a configuration of fitting into the circumference of the recess of the Petri dish body in a removable fashion. And, the circular recess of a Petri dish body is filled with an agar medium or the like, which is covered with the lid. The inside thereof is kept in a sterilized state (Patent Literature 1).

In addition, for the purpose of hygiene control of production facilities for food products or pharmaceutical products or the like, a device for microorganism detection in which an adhesive layer is formed on the top surface of a cover sheet covering a hydrous agar medium with a concentration of not less than 2.5% (Patent Literature 2). This is done with the view of a problem that the number of the microorganisms changes according to the amount of exudate fluid of a solid medium when microorganisms collected onto an adhesive sheet are cultured by laminating the adhesive sheet or the like. By using the hydrous agar medium with a concentration of not less than 2.5%, migration of microorganisms by the exudate fluid contained in the solid medium can be prevented and changes in the number of the microorganisms to be detected can be prevented.

Meanwhile, a wipe-up test kit is available, which kit has a container body in which a dilution solution is accommodated, an cap which tightly seals the opening section of this container body and is equipped in an attachable and detachable fashion, a cotton-tipped swab handle fixed or integrated to this cap, a swab which is placed at the end of this cotton-tipped swab handle and immersed in a dilution solution in a state where the container is sealed tightly with the cap. This wipe-up kit is characterized in that an extension rod can be attached to the above cap (Patent Literature 3). In a wipe-up test method, the surface of an instrument subjected to the test or the like is wiped using the cotton-tipped swab moistened with sterilized phosphate buffered saline or the like and sterilized; and then the resulting cotton-tipped swab is put in a storage bottle to obtain a sample test solution. It is claimed that the attachment of the extension rod makes wipe-up easier.

In addition, a test method in which microorganisms on a test surface are wipe up with a fiber layer to be collected and then cultured in a water-soluble high molecular weight compound layer is available (Patent Literature 4). It is a wipe-up test method for microorganisms characterized in that a fiber layer which wiped up the surface of an object to be inspected is placed on or pasted to a medium whose upper layer has the water-soluble high molecular weight compound layer and culturing is carried out to check if microorganisms are present. A method for collecting bacteria in which a hydrous matrix in a medium for microorganisms comprising the hydrous matrix and the water-soluble high molecular weight compound layer is brought into direct contact with an object to be inspected has been invented with the view of problems that a medium component or the like is attached to the object to be inspected or the like. The method involves separating the fiber layer from the water-soluble high molecular weight compound layer and wiping up the object to be inspected with the above-mentioned fiber layer, followed by culturing this fiber layer in the water-soluble high molecular weight compound layer.

Moreover, air samplers for airborne bacteria are on sale from a variety of companies. But in the case of clean environment, a longer sampling time is required. When a Petri dish is left uncovered for a long period of time, a water component in the medium reduces and the medium cracks or dries, which may affect bacterial growth (Patent Literature 5)

CITATION LIST

Patent Literature

Patent Literature 1: Unexamined Japanese Patent Application Kokai Publication No. 2008-278772
Patent Literature 2: Unexamined Japanese Patent Application Kokai Publication No. 2006-230315
Patent Literature 3: Unexamined Japanese Patent Application Kokai Publication No. 2008-101971
Patent Literature 4: Unexamined Japanese Patent Application Kokai Publication No. 2001-333796
Patent Literature 5: Unexamined Japanese Patent Application Kokai Publication No. 2000-304663

SUMMARY OF INVENTION

However, in the method described in Patent Literature 1 in which an agar medium is used as a medium for stamping, the agar medium is required to be brought into contact with an area to be inspected. The area to be inspected may be contaminated with a medium component or water and, in some cases, the contacted area may become a breeding area for bacteria. In order or avoid such a residual medium, washing after collection of bacteria is required, which complicates operations. Also, in a method of collecting bacteria by bringing an agar medium into contact with an area to be inspected, efficiency for collection of microorganisms is low and 50% or less of bacteria attached to the area to be inspected can be merely collected. In particular, when cloth such as a lab coat or the like is an area to be inspected, a medium component and water is absorbed by the cloth, which may causes contamination of the lab coat as well as decrease in an efficiency for collection of bacteria attached to the cloth.

Further, in Patent Literature 1 and Patent Literature 2, an agar medium is used as a medium component. Agar turns into a sol when heated to around 100° C. and turns into a gel at around 45 to 50° C. There is a tendency that solidified water is seeped out of a gel product. Because of this, when the agar medium is used for culturing bacteria having flagella or the like, the bacteria may migrate by the solidified water and may cause troubles in observing colonies. In addition, the agar contains unsaturated fatty acids and is thus not suitable for culturing bacteria sensitive to actions of the unsaturated fatty acids.

Moreover, when the agar is covered with an adhesive layer of the cover sheet, adhesive foreign substances may easily cause unwanted incorporation of air bubbles and may lower visibility.

Further, in the swab method by Patent Literature 3, a cotton-tipped swab in conjunction with a dilution solution was equipped in a vessel. After a object to be inspected was wiped up using a swab immersed in the above-mentioned dilution solution, the swab was collected in the vessel. Only a part of the dilution solution containing the collected bacteria is aliquoted in an inspection vessel such as a Petri dish and subjected to culturing and thus, in general, the number of cultured microorganisms decreases. Additionally, the swab immersed in the dilution solution is brought into direct contact with the object to be inspected and thus the object to be inspected may be contaminated.

Furthermore, the measurement method of Patent Literature 4 has in common with that of Patent Literature 3 in that a moistened fiber layer is used for wiping. A hydrous fiber layer is brought into direct contact and a object to be inspected may be contaminated. Similar to the stamp medium described in Patent Literature 1, in cases where the object to be inspected is an article absorbing water, a sample object absorbs water and, in some cases, an efficiency for collection of bacteria attached to an object to be inspected may further decrease.

Meanwhile, it is preferred that a microorganism culture sheet allow simple and convenient collection and processing of a sample, as well as be compact. The medium for stamping described in Patent Literature 1 requires predetermined thickness because a hydrous agar medium is used. Agar is not cold water soluble powder or a water-soluble high molecular weight compound. Thus, it is difficult to prepare a dry medium. Accordingly, development of a compact, sheet-type product using a dry culture layer is desired.

Bacteria are cultured in a separate medium after collected using a swab moistened with a dilution solution in Patent Literature 3 and using a fiber layer moistened with sterilized water or the like in Patent Literature 4. When bacteria are collected for the purpose of hygiene control of production facilities for food products or pharmaceutical products, if collection of bacteria using an adhesive layer of cover sheet becomes possible, contamination of test surface resulting from collection of bacteria using the moistened article can be prevented. In addition, use of a dry culture layer to prepare a hydrous culture layer by giving a gelling solution thereto at the time of culturing allows easier storage prior to use and trimming weight. Furthermore, a setting plate sampling method using an agar medium or a collision method are conventionally carried out for a test of airborne microorganisms. Attempt of a long-hour collection results in moisture evaporation from the agar, which affects bacterial growth. Thus, there has been no choice but to use an expensive membrane filter or the like for a test for an indoor room with higher cleanliness.

With the view of the above problems, an object of the present invention is to provide a microorganism culture sheet by which microorganisms are readily collected from a test surface, which sheet having a dry culture layer where the collected bacteria may be cultured and capable of detecting the microorganisms with high accuracy, wherein airborne microorganisms can be cultured even when a collection period is longer in a test for airborne microorganisms, the sheet being compact in size.

The present invention found, as a result of examining details of a microorganism culture sheet, that microorganisms can be collected with high collection efficiency by laminating an adhesive layer and a release film on the inner face of a cover sheet and peeling off the release film to bring the adhesive layer into contact with a test surface; microorganisms to be collected can be cultured on a culture layer by dropping a gelling solution such as a physiological saline, sterilized purified water, or the like to a dry culture layer with composition for microorganisms to be tested and subsequently covering it with the cover sheet; further a contact area can be kept clean due to no contamination of medium component and no requirement of giving water; and unwanted incorporation of air bubbles can be prevented and significantly higher visibility than an agar medium can be secured by bringing the adhesive layer of the cover sheet into contact with the culture layer via the gelling solution, thereby completing the present invention.

Accordingly, the present invention is to provide a microorganism culture sheet comprising a base sheet, a dry culture layer formed on the above-mentioned base sheet, and a cover sheet which covers the above-mentioned dry culture layer, wherein an adhesive layer and a release film are laminated on the inner surface of the above-mentioned cover sheet.

Also provided is a microorganism culture kit comprising a microorganism culture sheet comprising a base sheet, a dry culture layer formed on the above-mentioned base sheet, and a cover sheet which covers the above-mentioned dry culture layer, wherein an adhesive layer and a release film are laminated on the inner surface of the above-mentioned cover sheet, and a gelling solution for the above-mentioned dry culture layer.

Also provided is a method for culturing bacteria collected on the adhesive layer of the above-mentioned microorganism culture kit, which method is having the step of collecting bacteria on the above-mentioned adhesive layer, the step of turning the dry culture layer into a gel by adding the above-mentioned gelling solution and covering with the adhesive layer of the cover sheet, and culturing after completion of the gelling.

Also provided is a method for culturing bacteria for a test for airborne microorganisms, which method is having the step of peeling off the release film, pasting the sheet in a Petri dish with the adhesive layer of the cover sheet up to place and setting the Petri dish in an air sampler, carrying out sampling for a predetermined period of time, adding the above-mentioned gelling solution to the dry culture layer and covering the culture layer with the adhesive layer of the cover sheet; and culturing after completion of the gelling.

In cases where measurement of falling bacteria is carried out without using the air sampler, the sheet may be left to stand with the adhesive layer of the cover sheet up for a predetermined period of time and subsequently the above operations may be carried out.

Figure 12:
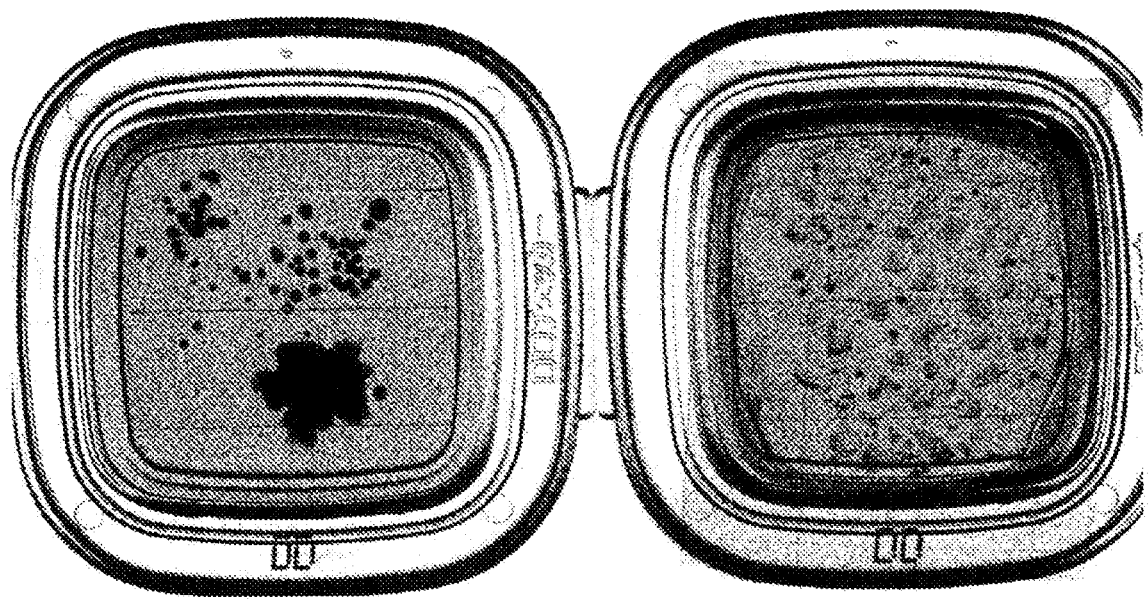

According to the present invention, microorganisms can be readily and quantitatively collected only by bringing an adhesive layer formed on the inner surface of a cover sheet into a test surface, leading to a simpler and more convenient use. With using an adhesive layer with little water, the test surface is thus hardly contaminated by culture medium.

According to the present invention, compared with a test method in which measurement is carried out, as described in Patent Literature 3, by taking 1 mL out of wipe-up 10 mL of dilution solution, bacteria in that part can be more accurately measured.

According to the present invention, a dry culture layer is given a gelling solution in drops and then covered with an adhesive layer of cover sheet on which bacteria are collected, which allows wet spreading of the gelling solution to the adhesive layer and consequent reduction of unwanted incorporation of air bubbles. Because of no air bubble-induced decrease in visibility, clear distinction between bacteria and contaminants other than bacteria, air bubbles, or the like, and improved visibility, highly accurate detection of microorganisms can be attained.

According to the present invention, because airborne microorganisms can also be collected by an adhesive layer, drawbacks of drying a medium which has been problematic in a setting plate sampling method and a collision method using a conventional agar medium can be solved and thereby the sheet of the present invention can be preferably used.

According to the present invention, in cases where a frame layer is formed on a base sheet, administration of a gelling solution such as physiological saline or the like does not cause collapse of the frame layer; and it remains stable. Ease of operation and stability is thus excellent.

In the microorganism culture sheet of the present invention, the base sheet and the cover sheet can be prepared using transparent materials; and microbial colonies can be measured using light coming from the back and/or lateral sides, which widens choice of a use of the method.

In addition, because the microorganism culture sheet of the present invention has the cover sheet which covers the dry culture layer, contamination by falling bacteria or the like can be prevented during a culturing operation. At the same time, evaporation of moisture in the dry culture lay after the administration of the gelling solution can be prevented.

Furthermore, according to the present invention, compactness in size is obvious. It also contributes to reduce waste after use.

BRIEF DESCRIPTION OF DRAWINGS

FIG. 1 is a plan view (a), an A-A' line sectional view (b), and a B-B' line sectional view (c) of an example of a microorganism culture sheet recited in the present invention, which sheet comprising a base sheet, a dry culture layer, and a cover sheet, and the figure shows a mode in which, in the cover sheet (40), an adhesive layer (43) is laminated on the inner surface facing the above-mentioned dry culture layer (30), and the above-mentioned adhesive layer (43) is further covered with a release film (45), and a round shaped culture layer is formed at a substantially center of the base sheet;

FIG. 2 is a sectional view showing an example of a microorganism culture sheet recited in the present invention, which sheet comprising a base sheet, a dry culture layer and a cover sheet. FIG. 2(*a*) shows a mode in which the base sheet has a multilayer structure and FIG. 2(*b*) is a figure showing a mode in which the dry culture layer has the multilayer structure;

FIG. 3 is a plan view (a), an A-A' line sectional view (b), and a B-B' line sectional view (c) of an example of a microorganism culture sheet recited in the present invention, which sheet comprising a base sheet, a dry culture layer, a frame layer, and a cover sheet, and the figure shows a mode in which, a square base sheet (10), the dry culture layer (30) is formed at a substantially center of, an adhesive layer (43) is laminated on the inner surface of the cover sheet (40) facing the above-mentioned dry culture layer (30), the above-mentioned adhesive layer (43) is covered with a release film (45), the frame layer (20) is formed on the circumference of the above-mentioned dry culture layer (30), the square cover sheet (40) is installed so as to cover these;

FIG. 4 is a sectional view showing an example of a microorganism culture sheet recited in the present invention, which sheet comprising a base sheet, a dry culture layer, frame layer and a cover sheet. FIG. 4(*a*) shows a mode in which the base sheet has a multilayer structure and FIG. 4(*b*) is a figure showing a mode in which the dry culture layer has the multilayer structure;

FIG. 5 is a figure illustrating a method for producing a microorganism culture sheet recited in the present invention, which sheet comprising a base sheet, a dry culture layer, a cover sheet on which an adhesive layer and a release film are laminated. A plan view (a), a line sectional view ((b) and (c)) show a mode in which the base sheet is connected with the cover sheet, the dry culture layer is formed on the base sheet, the adhesive layer and the release film are laminated on the cover sheet, and then the cover sheet is folded to form the microorganism culture sheet;

FIG. 6 is a sectional view of a microorganism culture sheet recited in the present invention comprising a base sheet, a dry culture layer, and shows a mode in which a base sheet on which an adhesive layer and a release film are laminated is fixedly installed on the cover sheet via a double face adhesive tape (50);

FIG. 7 is a sectional view of a microorganism culture sheet recited in the present invention comprising a base sheet, a dry culture layer and a cover sheet on which an adhesive layer and a release film are laminated, and shows a mode in which the dry culture layer is formed on the entire surface of the base sheet and the cover sheet is fixedly installed on the base sheet by a double face adhesive tape (50);

FIG. 8 is a outer appearance perspective view of a microorganism culture sheet recited in the present invention, the sheet comprising a base sheet, a dry culture layer and a cover sheet;

FIG. 9 is a figure showing colonies detected in Example 1;

FIG. 10 is a figure showing colonies detected in Comparative Example 2;

FIG. 11 is a figure showing colonies detected in Example 4; and

FIG. 12 is a figure showing colonies detected in Comparative Example 3.

DETAILED DESCRIPTION OF THE PRESENTLY PREFERRED EMBODIMENTS

The first of the present invention is a microorganism culture sheet comprising a base sheet, a dry culture layer formed on the above-mentioned base sheet, a cover sheet that covers the above-mentioned dry culture layer, wherein an adhesive layer and a release film are laminated on the inner surface of the above-mentioned cover sheet.

Because the adhesive layer and the release film are laminated on the cover sheet, by peeling off the release film and bringing the adhesive layer into contact with a test surface, microorganisms can readily be collected in a quantitative fashion. On the top of that, because the culture layer is formed using a dry culture layer, compactness in size and excellent shelf stability are attained. The frame layer may be formed on the base sheet and the dry culture layer may be formed on the inner surface thereof. When the frame layer is formed on the base sheet by using a hydrophobic resin, the frame layer does not collapse upon administration of a gelling solution such as physiological saline or the like. Thus, operations can be stably carried out. The dry culture layer may be formed on the above-mentioned base sheet by patterning. Combination the adhesive layer of the cover sheet with a gelling solution and the dry culture layer prevents air bubbles from unwantedly incorporating there and enables culturing, which improves visibility after culturing. The present invention will now be described in detail below.

(1) Composition of Microorganism Culture Sheet

An example of a preferred mode of a microorganism culture sheet of the present invention is shown in FIGS. 1(a), (b), and (c). FIG. 1(a) is a plan view; FIG. 1(b) is an A-A' line sectional view of FIG. 1(a); and FIG. 1(c) is a B-B' line sectional view of FIG. 1(a).

FIG. 1 shows a mode in which a dry culture layer (30) is formed at a substantially center of a rectangle base sheet (10) and a rectangle cover sheet (40) is mounted so as to cover the above-mentioned dry culture layer (30). In the above-mentioned cover sheet (40), an adhesive layer (43) is laminated on the inner surface facing the above-mentioned dry culture layer (30); and the above-mentioned adhesive layer (43) is further covered with a release film (45). As shown in FIG. 1(c), the above-mentioned cover sheet (40) is fixed to the base sheet (10) via the adhesive layer (43).

Figure 2:
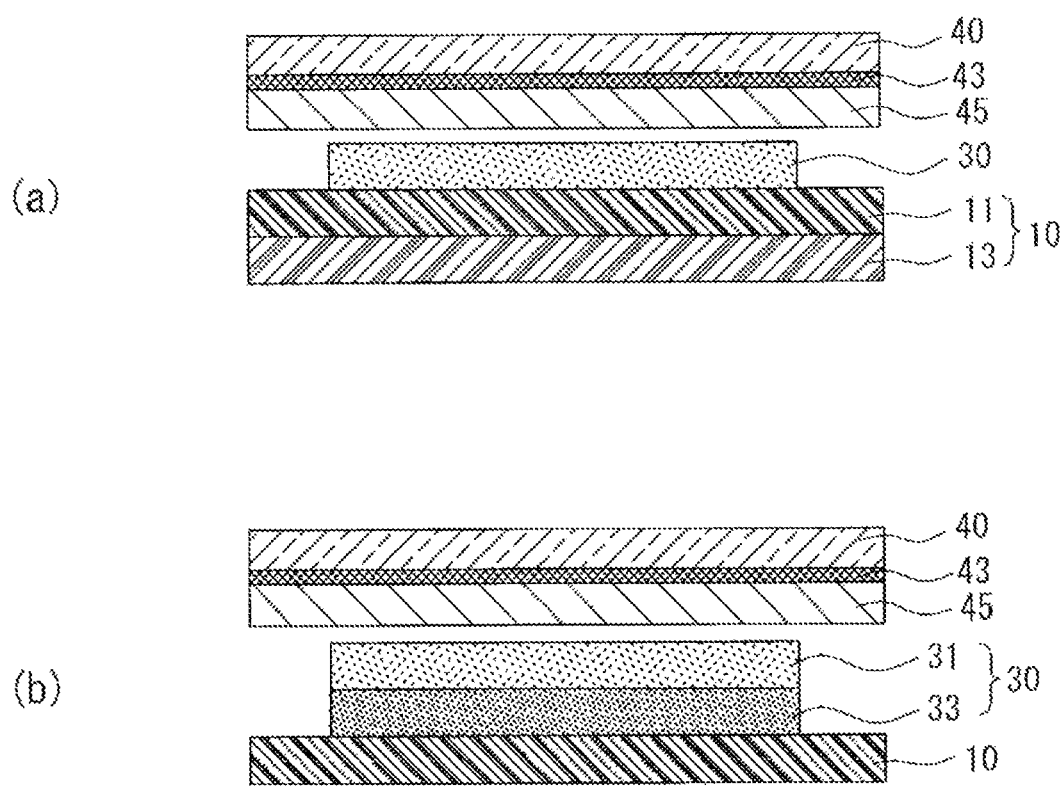

In the present invention, the dry culture layer (30) may be formed on the base sheet (10) by patterning. As shown in the sectional view of FIG. 2(a), the base sheet (10) may be a multilayer sheet comprising two layers of a base sheet (11) and a base sheet (13) and may further be a multilayer sheet with another layer except plastic being laminated. Additionally, as shown in FIG. 2(b), the dry culture layer (30) may be composed of multiple layers with two or more layers. The shape of the dry culture layer (30) prepared by patterning is not limited to a circle shape shown in FIG. 1 and may be square, rectangle, other polygons, or irregular. This point is applied similarly to the shape of the base sheet (10).

Figure 3:
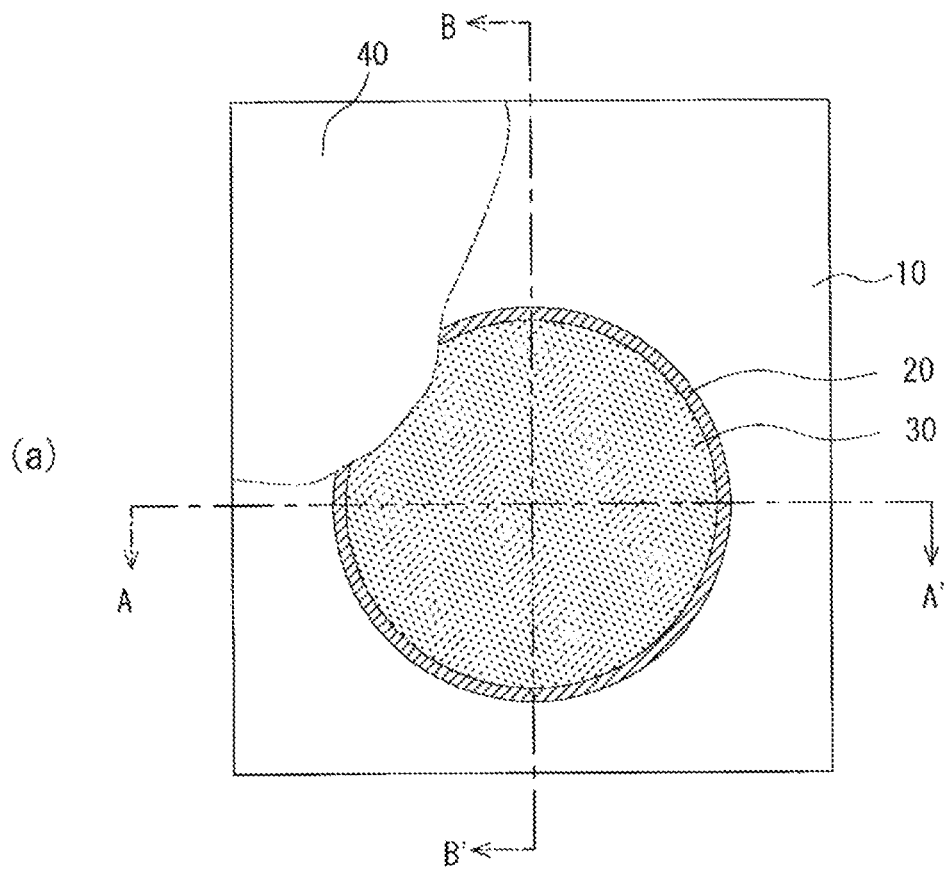
Figure 3:
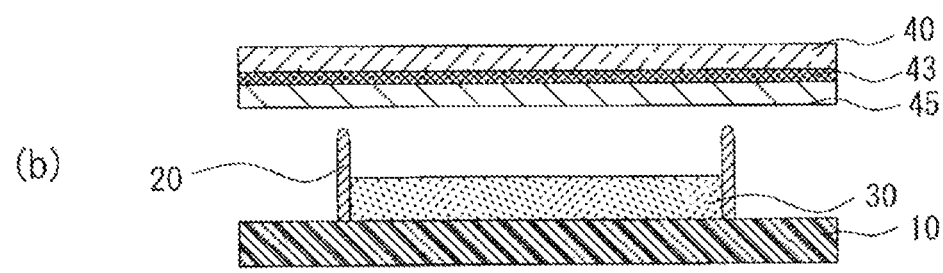
Figure 3:
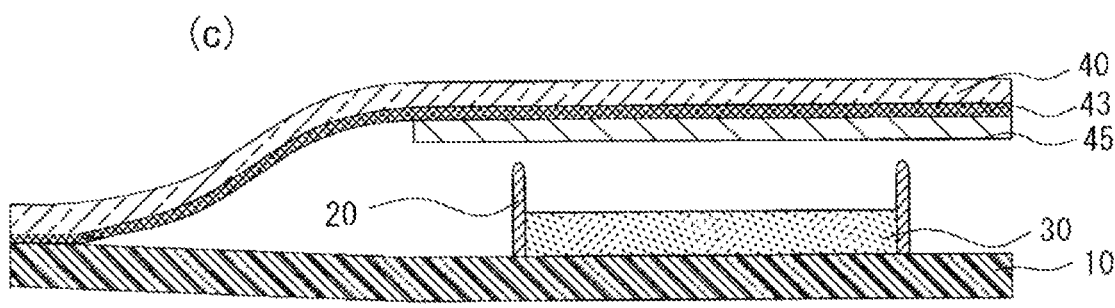

In addition, the microorganism culture sheet of the present invention may, as shown in FIG. 3, be one in which the frame layer (20) is formed on the base sheet (10) and the dry culture layer (30) is formed inside thereof. Formation of the frame layer (20) on the circumference of the dry culture layer (30) retains a gelling solution such as a physiological saline or the like to a predetermined range and prevents a leak of the gelling solution. Accordingly, the dry culture layer is not required to be present outside the frame layer (20). An example of preferred mode of a microorganism culture sheet having such a frame layer (20) is shown FIGS. 3(a), (b), and (c). FIG. 3(a) is a plan view; FIG. 3(b) is an A-A' line sectional view of FIG. 3(a); and FIG. 3(c) is a B-B' line sectional view of FIG. 3(a).

FIG. 3 shows a mode in which the dry culture layer (30) is formed at a substantially center of a rectangle base sheet (10); the frame layer (20) is formed on the circumference of the above-mentioned dry culture layer (30); and the rectangle cover sheet (40) is mounted so as to cover this. In the above-mentioned cover sheet (40), an adhesive layer (43) is laminated on the inner surface facing the above-mentioned dry culture layer (30); and the above-mentioned adhesive layer (43) is further covered with a release film (45). By forming the dry culture layer (30) directly on the base sheet (10) and preparing the frame layer (20) using a hydrophobic resin, the frame layer (20) does not break up by the gelling solution, even when a gelling solution is administered onto the dry culture layer (30).

In addition, the formation of frame layer (20) enables the gelling solution to uniformly spread all over the entire region of the dry culture layer (30) within frame layer (20) without specialized instruments only by dropping the gelling solution onto the dry culture layer (30) surrounded by the frame layer (20) and by putting down the cover sheet (40) to cover the adhesive layer (43) of the cover sheet (40), which leads to excellent ease of operation.

Figure 4:
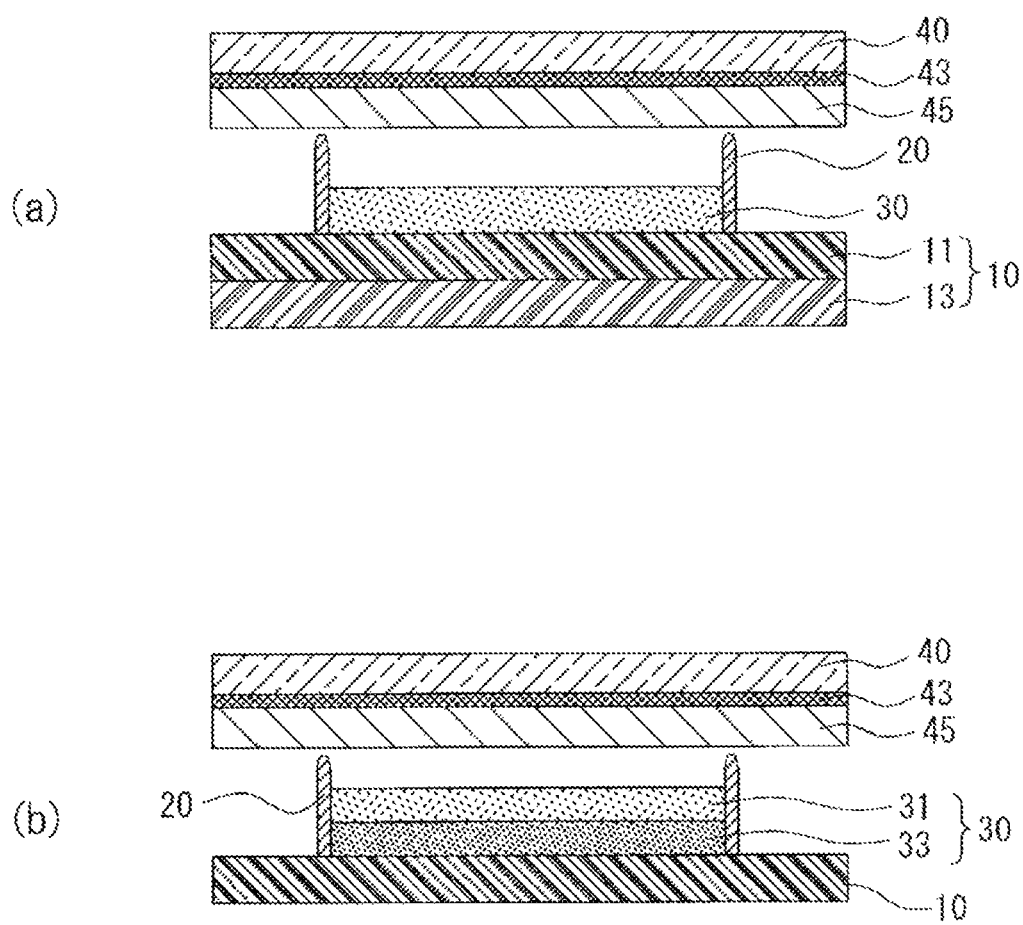

In the present invention, it is preferred that the frame layer be formed on the base sheet (10) using a hydrophobic resin. Because of this, as shown in the sectional view of FIG. 4(a), the base sheet (10) may be composed of a multilayer sheet comprising of the base sheet (11) and the base sheet (13) and may further be one with another layer except plastic being laminated. Also, as shown in the above-mentioned FIG. 4(b), the dry culture layer (30) may be composed of multiple layers with two or more layers. In the present invention, the frame layer comprising a hydrophobic resin is preferably formed on the surface of the base sheet (10) and the dry culture layer (30) is not present between the base sheet (10) and frame layer. Thereby, the frame layer comprising a hydrophobic resin can be formed stably on the base sheet (10) and wasting medium materials can be avoided. In the present invention, the diameter of equivalent circle of the above-mentioned dry culture layer (30) is 20 to 80 mm and more preferably 30 to 70 mm. The amount of gelling solution to be dropped onto the microorganism culture sheet is in general 1 ml. This is adequate for the gelling solution to be absorbed into the above range.

In general, the height of frame layer (20) is prepared to be higher that the height of the dry culture layer by 100 to 1200 μm, preferably by 200 to 1000 μm, and more preferably by 300 to 800 μm. When the height is in the above range, a gelling solution is promptly diffused within the frame layer (20) without leaking the gelling solution from a dry culture layer (30) and creating an air space when the gelling solution is administered onto the dry culture layer (30). And the cover sheet (40) can immediately cover without waiting for gelling solution to be absorbed into the dry culture layer, which can lead to improved working efficiency.

In addition, the width of the frame layer is not limited to an uniform width and the narrowest part is preferably 0.5 to 5.0 mm in width and more preferably 1.0 to 3.0 mm This is because adhesion with the cover sheet is excellent when the width is in the above range.

In the present invention, as long as the frame layer comprising a hydrophobic resin is formed on the circumference of the dry culture layer of the base sheet, it does not limited to a single frame layer and may be a frame layer comprising a multiplex frame in which other frame layers are formed outside the above frame layer.

Figure 5:
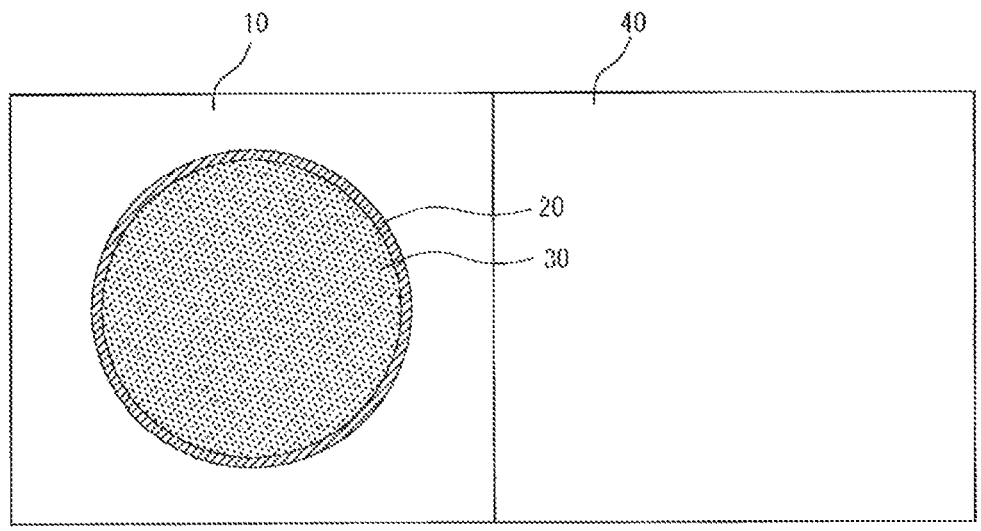
Figure 5:
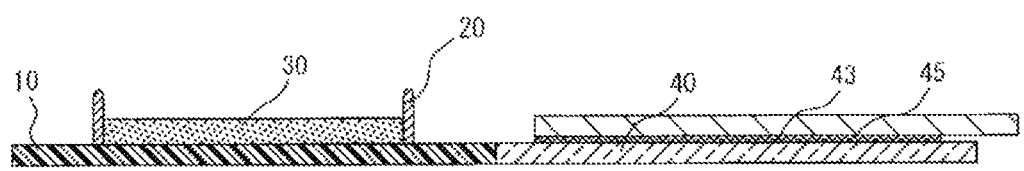
Figure 5:
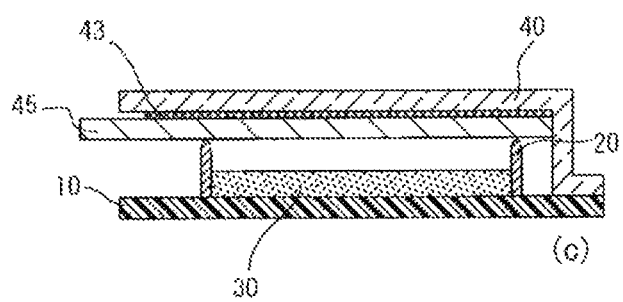
Figure 6:
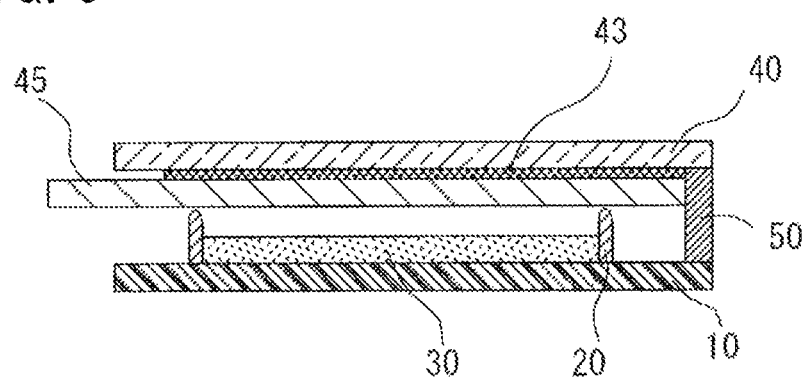

Furthermore, as shown in FIG. 5(*c*), the cover sheet (40) may be fixedly installed on the base sheet (10). At that time, as shown in FIG. 6, the cover sheet (40) may be fixedly installed on the base sheet (10) via a double face adhesive tape (50). The microorganism culture sheet of the present invention may one in which the dry culture layer (30) is formed on the entire surface of the base sheet (10) and may be one in which the dry culture layer contains a nonwoven fabric.

(2) Base Sheet

A base sheet used in the present invention is required to have solvent resistance and printability. In addition, as a microorganism culture sheet, water resistance is also required. Heat resistance enabling the sheet to withstand in a drying treatment at the time of formation of a dry culture layer is also required. The base sheet may be a monolayer or may be a lamination sheet having two or more layers.

In cases where the base sheet is the monolayer, a plastic sheet such as, for example, polyester, polyethylene, polypropylene, polystyrene, polycarbonate, polyvinyl chloride or the like can be preferably used. Because such a plastic sheet is excellent in transparency, microbial colonies can be observed using light coming through the base sheet and visibility can be improved. In addition, a range of choices for measurement method procedure can be expanded. Concretely, the microorganism culture sheet of the present invention is for observing or counting colonies grown in the dry culture layer; and with the base sheet or the cover sheet being transparent, observation can be carried out using light coming through the back of the microorganism culture sheet or using light coming from the lateral side thereof. Accordingly, the observation and counting can be carried out both from the cover sheet side and from the base sheet side. Further, one developing white color by foaming and one providing any color can also be used. It depends on the specie of bacteria cultured but some are not limited to be transparent. Coloring may facilitate counting the colonies grown and coloring can be appropriately selected.

An example of the lamination sheet includes one in which two or more of the above plastic sheets are laminated. Also preferably used are a lamination sheet in which the above plastic sheet is laminated with a paper base and a lamination sheet in which the paper base is coated with a synthetic resin, or the like. An example of such a lamination sheet includes a lamination sheet made up of a polyethylene film and the paper base.

Furthermore, a synthetic paper prepared using a synthetic resin as a major raw material and molded like papers can be used as the base sheet. Examples of such a synthetic paper include trade name "YUPO" manufactured by Yupo Corporation, "Crisper" manufactured by Toyobo Co., Ltd., and the like.

For the purpose of improving adhesion with the above dry culture layer, the base sheet used in the present invention may be in advance subjected to surface treatment at one side formed a dry culture layer. Examples of such a surface treatment include corona discharge treatment, ozone treatment, low temperature plasma treatment using oxygen gas, nitrogen gas, or the like, glow discharge treatment, oxidation treatment in which a chemical agent or the like is used for treatment, other pretreatment and the like.

In addition, the surface of the base sheet used in the present invention can be in advance coated with an anchor coating agent and subjected to surface treatment. Examples of such an anchor coating agent include isocyanate-based (urethane-based), polyethyleneimine-based, polybutadiene-based, organic titanium-based and other anchor coating agents. More preferred is one having, as a major component, a polyether polyurethane-based resin, a polyester-based polyurethane-based resin, or a polyacrylate polyurethane-based resin, which is obtained by reacting multifunctional isocyanate including aromatic polyisocyanate such as tolylenediisocyanate, diphenyl methane diisocyanate, polymethylene polyphenylene polyisocyanate or the like; or aliphatic polyisocyanate such as hexamethylene diisocyanate, xylylene diisocyanate, or the like; with hydroxyl group-containing compound such as polyether-based polyol, polyester-based polyol, polyacrylate polyol or the like.

It is preferred that the base sheet lie flat without curling. The thickness thereof is not particularly restricted and usually 25 to 1500 μm and more preferably 50 to 500 μm.

A square print pattern may be in advance printed on the base sheet using an ink that is insoluble to water and does not affect growth of microorganisms. This is because, when a lot of colonies are formed, square printing allows determination of the approximate total number of bacteria by counting the number of the bacteria in several squares and dividing them proportionally. The printing process of the print is not particularly restricted and may be any. Gravure printing or the like is preferred because a wide range of choices for coloring agents, resins, solvents, and the like is available. As for the size of the square, about 1 cm square is appropriate.

(3) Dry Culture Layer

In the microorganism culture sheet of the present invention, the dry culture layer is fixedly set up on the base sheet. When microorganisms collected by the adhesive layer are cultured in the dry culture layer, the above-mentioned dry culture layer is required to contain water appropriate to growth of the microorganisms and, in general, a conventionally known water-soluble high molecular weight compound capable of gelling, thickening or the like can be widely used. A general term for such a material is referred to as a gelling agent in the present invention. The dry culture layer may also contain nutrient components and others. Furthermore, the dry culture layer may also be made up of nonwoven fabrics.

(i) Gelling Agent

Examples of a gelling agent composing a dry culture layer of the present invention include a water-soluble high molecular weight polysaccharide such as carrageenan, guar gum, xanthane gum, locust bean gum, algin, starch and a derivative thereof, a cellulose derivative (for example, carboxymethyl cellulose, hydroxy alkyl cellulose, and the like) or the like; and a water soluble polymer such as a copolymer of polyvinyl alcohol (PVA), denatured PVA and unsaturated dicarboxylic acid, polyacrylic acid and a derivative thereof, polyether (for example, polyethylene glycols, polypropylene glycol and the like) or the like. The guar gum is particularly preferred because it shows very high viscosity at low concentrations. Thus a small amount of it allows setting environments appropriate to growth of bacteria. Also, in consideration of viscosity, strength, growth ability of bacteria, two or more gelling agents can be mixed to use.

(ii) Nutrient Component

In addition to the above gelling agent, nutrient components can be blended in a dry culture layer of the present invention.

Example of the nutrient component to be used include a mixture of yeast extract, peptone, and glucose, a mixture of meat extract and peptone, a mixture of peptone, soybean peptone, and glucose, and the like for a test for general viable bacteria; peptone, ammonium iron citrate, lactose and the like for a test for *Escherichia coli* and *Escherichia coli* group; a mixture of meat extract, peptone, mannite, and egg yolk, a mixture of peptone, meat extract, yeast extract, sodium pyruvate and the like for staphylococcal bacteria; a mixture of yeast extract, peptone, sucrose, sodium thiosulfate, sodium citrate and the like for vibrio; a mixture of bovine brain extract, heart extract, peptone, glucose and the like for enterococcus bacteria; a mixture of peptone and glucose, a mixture of yeast extract, glucose, a mixture of potato extract, and glucose for fungus. One or more can be selected from these depending on microorganisms to be grown. The selected are mixed to be used.

(iii) Other Components Such as Chromogenic Indicator, Selective Agent, Substrate, or Buffering Agent (pH Adjusting Agent)

In addition to the above gelling agent, other component such as a chromogenic indicator, a selective agent, a substrate can be blended to form the dry culture layer of the present invention.

The chromogenic indicator is metabolized by microorganisms growing in a culturing process and their colonies are colored, and thus brings out an effect of making count of the number of the colonies extremely easier. Concrete examples of such a chromogenic indicator include triphenyl tetrazolium chloride (hereinafter referred to as TTC), tetrazolium salt such as p-tolyl tetrazolium red, tetrazolium violet, petetolyl tetrazolium blue; or the like and a pH indicator such as neutral red mixture, phenol red, bromothymol blue, thymol blue mixture or the like. As microorganisms grow, the color is developed or changes, which facilitates growth of the microorganisms to be observed. Also, addition of a chromogenic substrate or a fluorescence enzyme substrate for an enzyme carried by a certain microorganism enables detection of the certain microorganism.

Furthermore, a selective agent that inhibits growth of microorganisms other than microorganisms to be observed may also be added; and examples of such as a selective agent to be used include an antibiotic such as an antibiotic substance, a synthetic antimicrobial agent, or the like, colorants, detergent, inorganic salt or the like. Examples of the antibiotic include meticillin, cefmetazole, cefixime, ceftazidime, cefsulodin, bacitracin, polymyxin B, rifampicin, novobiocin, colistin, lincomycin, chloramphenicol, tetracycline, streptomycin and the like; and examples of the synthetic antimicrobial agent include sulfonamide, nalidixic acid, olaquindox and the like. Also, examples of the colorant include crystal violet, brilliant green, malachite green, methylthioninium chloride and the like, each of which has an antimicrobial action or sterilization action. Additionally, examples of the detergent include Tergitol 7, dodecyl sulfate, laurylsulfate, polyoxyethylene (20) sorbitan monooleate (Tween 80), polyoxyethylene (20) sorbitan monolaurate (Tween 20) and the like. In addition, examples of the inorganic salt include selenite, tellurite, sulfite, sodium azide, lithium chloride, oxalate, a high concentration of sodium chloride, and the like. Besides, taurocholate, glycine, bile powder, bile salt, deoxycholate, a high concentration of saccharide or the like can be used. A buffering agent has an action of bring the pH of a sample solution back to 7.0 in a case where it is tremendously different from 7.0. This is because a pH at which bacteria readily grow is a neutral pH of approximately 7.0. An example of the buffering agent include a combination of disodium hydrogen phosphate, sodium dihydrogen phosphate, dipotassium hydrogen phosphate, potassium dihydrogen phosphate, sodium chloride and the like.

It depends on the type of the chromogenic indicator, but some show highly visible color at the time of a sterilization treatment. Instead of being included in a dry culture layer, the chromogenic indicator may be included in a gelling solution described later and used to obtain a medium which develops color.

The dry culture layer of the present invention may contain at least the gelling agent (i) and may further contain the nutrient component (ii) or other components (iii) such as a chromogenic indicator, a selective agent, substrate, or the like. A certain combination between the chromogenic indicator and the selective agent may cause a reaction by mixing. These can be contained in a separate layer to prevent the mixing reaction. In addition, by forming the chromogenic indicator in the most upper layer, visibility of colonies can be improved.

(iv) Composition of Dry Culture Layer

As for a dry culture layer used in the present invention, one containing at least the above gelling agent (i) may be required to be formed on the base sheet. One containing, in addition to the gelling agent, a nutrient component (ii) and other components (iii) such as a chromogenic indicator, a selective agent, substrate or the like may also be formed. The dry culture layer may have multiple layers with two or more layers. In addition, the dry culture layer may be formed on the entire surface of the base sheet or may be formed by patterning. The dry culture layer may further contain nonwoven fabrics or the like. As nonwoven fabrics, preferred is a materials such as synthetic fiber (for example, nylon, polyester (in particular, one which has a hydrophilic treatment), polyacrylonitrile, polyolefin (in particular, one which has a hydrophilic treatment), polyurethane or the like), semi-synthetic fiber (for example, rayon or the like), natural fiber (for example, cellulose, cotton, silk, wool (animal hair), or the like), inorganic fiber (for example, fiber glass or the like).

In the present invention, the thickness of the dry culture layer with a composition of containing no nonwoven fabrics is, when dried, 50 to 1000 μm and more preferably 200 to 600 μm. In addition, an amount of coating is, when dried, 5 to 400 g/m$^2$ and more preferably 100 to 300 g/m$^2$. Within the above range, a dry culture layer having an optimal viscosity for bacterial growth can be obtained.

(4) Cover Sheet

The present invention is characterized in that an adhesive layer and a release film are laminated on the inner surface of a cover sheet. The cover sheet used in the present invention has actions of preventing contamination by falling bacteria or the like in culture and concurrently preventing moisture evaporation of the dry culture layer after administration of gelling solution. Further, by removing the laminated release film, bringing the adhesive layer into contact with a test surface to collect bacteria, injecting a gelling solution to the dry culture layer, and contacting the adhesive layer with the dry culture layer, the bacteria can be cultured in the dry culture layer.

Because of this, the cover sheet preferably has flexibility which facilitates its contact with the test surface and the dry culture layer. Furthermore, while it has water proofness and steam impermeability, it is preferably transparent at the same time such that observation of colonies and count of the number of the colonies can be carried out through the cover sheet after culturing microorganisms.

For example, plastic such as polyester, polyamide, polystyrene, polycarbonate, polyvinyl chloride, or polyolefin such as polyethylene, polypropylene or the like; which is described for the above-mentioned base sheet, can be used. When ease of handling including opening and closing of cover sheet and the like is taken into consideration, a polyester film or a polyolefin film is particularly preferred. In addition, the cover sheet may be subjected to surface treatment such as corona discharge treatment which is described in a section on the base sheet. The cover sheet preferably has appropriate gas permeability according to the kind of microorganisms to be cultured, mainly oxygen permeability or oxygen impermeability and can be selected in consideration of this point.

It is preferred that the cover sheet secure appropriate flexibility which allows its contact with a test surface. Accordingly, the thickness of the cover sheet is preferably about 10 to 200 µm and further preferably about 20 to 70 µm. The cover sheet may take on any shape. But, in order to prevent unwanted bacteria from entering, it is required to have a size larger than the dry culture layer such that it can cover the dry culture layer.

The adhesive layer laminated on the inner surface of inside the cover sheet may be required to have adhesiveness sufficient to collect microorganisms on a test surface and may be required not to contaminate or deface a capture site. Examples of an adhesive composing such an adhesive layer include an acrylic-based adhesive, a rubber-based adhesive, and a silicone-based adhesive. In particular, from the viewpoint of fluorescent labeling property of microorganisms on a sticking surface, it is preferred that the adhesive have high transparency and a non-fluorescent property. The adhesive is more preferably an acrylic-based adhesive or a silicone-based adhesive.

Preferred concrete examples of such an acrylic-based adhesive include a copolymer in which one or more alkyl ester (meth)acrylates having a linear or branched alkyl group with 2 to 13 carbon atoms selected from, for example, ethyl (meth)acrylate, propyl (meth)acrylate, butyl (meth)acrylate, hexyl (meth)acrylate, octyl (meth)acrylate, nonyl (meth)acrylate, decyl (meth)acrylic acid and the like are copolymerized, as a primary monomer, with one or more hydrophilic monomers such as (meth)acrylic acid, itaconic acid, maleic acid, hydroxyethyl (meth)acrylate, methoxyethyl (meth)acrylate, ethoxyethyl (meth)acrylate, butoxyethyl (meth)acrylate, ethylene glycol (meth)acrylate, or the like. For improved an adhesion property (particularly, adhesive strength), also preferably used is one obtained by cross linking such a copolymer by carrying out treatment using a heat cross linker such as an isocyanate compound, organic peroxide or an epoxy group-containing compound, or irradiation treatment using an ultraviolet ray, a gamma ray, an electron beam, or the like.

Additionally, examples of the rubber-based adhesive include natural rubber, latex, a block copolymer between styrene-based polymer block and conjugated diene-based polymer block; a block copolymer between a styrene-based polymer block and a random copolymer block of a styrene-based monomer and a conjugated diene-based monomer, and hydrogenated product thereof, or the like. Besides, another example thereof include one obtained by combining a tackifier such as a terpene resin, an aliphatic hydrocarbon resin, an alicyclic hydrocarbon resin, a coumarone-indene-based resin, a rosin-based resin, a phenolic resin, a xylene-based resin, a styrenic resin, or the like; and a softener such as paraffinic oil, naphthenic oil or the like; with a base polymer such as natural rubber, styrene-isoprene-styrene copolymer, styrene-butylene copolymer, styrene-ethylene-butylene-styrene copolymer, ethylene-vinyl acetate copolymer, polyisobutylene, polyisoprene or the like.

Also, examples of the silicone-based adhesive include a silicone-based resin comprising partially cross-linked polysiloxane comprising a polymer component such as high molecular weight polydimethylsiloxane, polydimethyl diphenyl siloxane or the like, which polymer component has a silanol group (SiOH) in the terminus of a polymer having —SiO(CH$_3$)$_2$— as a repetition unit or the like, and a cross-linking component having three-dimensional silicate structure and a trimethylsiloxy group in the terminus; one comprising dimethyl siloxane and/or phenylmethyl siloxane as major components; one having polyorganosiloxane containing dimethyl siloxane units as a major component; or the like.

In cases where a water-soluble adhesive such as the above acrylic-based copolymerization product or the like is used, a plasticizer may, as necessary, be added within a range of 5 to 40 parts by weight per 100 parts by weight of the adhesive. The addition of the plasticizer can further increases flexibility and adhesiveness of the adhesive. The thickness of the adhesive layer is characterized by being 1 to 100 µm and more preferably 10 to 60 µm.

The release film is not particularly restricted as long as the adhesive layer can be readily peeled off before use. Examples thereof include a polyester film, a polyvinyl chloride film, a polyvinylidene chloride film, or the like whose surface contacting with the adhesive layer has a silicone treatment. The thickness of the release film is 10 to 200 µm and more preferably 20 to 100 µm.

In the microorganism culture sheet of the present invention, the above-mentioned adhesive layer may be covered with the release film after bacteria are collected by the above-mentioned adhesive layer. This is because, in cases where a large number of microorganism culture sheets are used to collect bacteria and a gelling solution is administered to these sheets at one time, it is convenient that the adhesive layer is temporarily covered again with the release film. For repeated covering described above, part of the release film may be fixedly installed to the cover sheet such that the film is not completely peeled off.

In cases where a square print pattern is not printed on the base sheet, the square print pattern may be printed in advance on the cover sheet using an ink that is insoluble to water and does not affect growth of microorganisms. The printing process of the print is preferably gravure printing or the like in the same way as the base sheet, because a wide range of choices for coloring agents, resins, solvents, and the like is available. As for the size of the square, about 1 cm square is appropriate.

(5) Frame Layer

In the present invention, a frame layer can be formed on the base sheet. This frame layer is prepared on the circumference of the dry culture layer formed on the base sheet. With the frame layer being formed, a gelling solution is promptly diffused to the frame layer when a gelling solution is administered to the dry culture layer and the dry culture layer is covered with the cover sheet, which enables operations to be performed in a short period of time. The gelling solution is absorbed into the dry culture layer inside the frame layer and the dry culture layer swells. Adhesion between the dry culture layer and the cover sheet prevents the dry culture layer from drying. Further, due to excellent adhesion with the cover sheet, any layer for colony formation is not required to be formed on the cover sheet and excellent visibility of colonies can be secured.

In the present invention, the height of frame layer formed on base sheet is prepared to be higher than the height of the dry culture layer by 100 to 1200 μm, more preferably by 200 to 1000 μm, and particularly preferably by 300 to 800 μm. In cases where it is below 100 μm, spread of the gelling solution after the diffusion cannot be inhibited, which may cause a leak. On the other hand, in cases where it is above 1200 μm, an excessive space is created at the upper part of the dry culture layer after absorption of water. Adhesion with the cover sheet becomes difficult to be secured and the dry culture layer becomes readily dried during culturing. Or, when the cover sheet and the dry culture layer are closely contacted temporarily, due to the excessive space, the cover sheet is detached from the dry culture layer, which may cause the dry culture layer to dry. With the height of frame layer being in the above range, the gelling solution can be absorbed into the dry culture layer and can spread all over the entire surface without a leak, which can leads to secured adhesion with the cover sheet.

In addition the above frame layer is formed on the base sheet. If the frame layer is formed on the base sheet, the frame layer may collapse after the dry culture layer absorbed the gelling solution. However, formation of the frame layer directly on the base sheet results in no infiltration of the gelling solution and avoidance of detachment of the frame layer or the like.

A hydrophobic resin used in the present invention repels water against spread of the administered gelling solution and prevents a leak during culturing. Because a gelling solution is an aqueous solution, a hydrophobic resin capable of repelling this is used. Therefore, almost if not all a hydrophobic resins can be used as a hydrophobic resin used in the frame layer unless they are a water soluble resin or a hydrophilic resin. These may be colored. An UV curable resin, a hot melt resin, a heat foaming ink, an UV foaming agent or the like can be suitably used.

Examples of the UV curable resin include acrylate-based and unsaturated polyester-based for a radical type, epoxy acrylate-based, oxetane-based, vinyl ether-based for a cation type, and the like; but is not limited thereto. Irradiation conditions for curing the UV curable resin is an integral light dose of 50 to 2000 mJ/cm$^2$ and more preferably 100 to 1000 mJ/cm$^2$.

In addition, as a hot melt resin, one having a softening point temperature of 120° C. or less, more preferably 100° C. or less can be preferably used. The reason for this is because the base sheet may curl at above 120° C. Examples of a hot melt resin which can be preferably used in the present invention include synthetic rubber-based such as urethane-based, polyamide-based, polyolefin-based, polyester-based, ethylene vinyl acetate-based, styrene butadiene rubber-based, urethane rubber-based or the like, but is not limited thereto.

As a hydrophobic resin, a heat foaming ink, an UV foaming agent or the like can be preferably used. For example, as a binder, an ink in which a polyolefin-based resin including a polyurethane-based resin, a polyamide-based resin, a polyvinyl chloride-based resin, a polyacrylate-based resin, a polyester-based resin, and chlorinated polypropylene; or rubber such as chlorinated rubber, cyclized rubber or the like can be used. If these inks have water repellency in addition to hydrophobicity alone, they are more preferred. From this point, an ink in which silicones or waxes are added to a resin is further preferred. In particular, a hydrophobic resin used in the frame layer has hydrophobicity and water repellency and is, at the same time, required to have high thickness of a coated film. It is effective for the above resin to be added with a conventionally known foaming agent or the like and used as a foaming ink. Examples of such an UV foaming ink include an ultraviolet ray curable foaming ink containing a foaming agent such as an inorganic foaming agent, an organic foaming agent, a liquid foaming agent or the like in an ultraviolet ray curable ink comprising at least a reactive diluents such as an acrylate-reactive diluents or a methacrylate-reactive diluents, a photo polymerizable oligomer such as an urethane acrylate photopolymerizable oligomer, a polyester acrylate photopolymerizable oligomer, an epoxy acrylate photopolymerizable oligomer, an acrylic-based photopolymerizable oligomer, a special photopolymerizable oligomer or the like, and a photoinitiator.

As an additive, an antifoaming agent, a polymerization inhibitor, a pigment dispersant or the like may be added to the above a hydrophobic resin. A colored pigment which is usually used can also be added in a range of below 15% by mass. When it is added above 15% by mass, there are concerns that foaming is inhibited, which may not be preferred.

In the present invention, all of the above can be suitably used as a hydrophobic resin with the UV curable resin or the hot melt resin being preferred. The reason for this is because formation of the frame layer requires patterning with uniform height, and these two resins can be, in an no solvent-based condition, readily subjected to profiling processing by spreading with a dispenser or the like, and can be readily cured by subsequent light irradiation or cooling, followed by patterning.

For formation of the frame layer with these, the above a hydrophobic resin may be subjected to patterning by printing, spreading, coating, or the like. Subsequently, irradiation of an ultraviolet ray (UV) is applied using a metal halide lamp, a mercury lamp, or the like, followed by cooling.

In addition, as for the frame layer, a product obtained by gouging out a hydrophobic material can be attached to the circumference of the dry culture layer to obtain the frame layer. Furthermore, there is a method comprising using an embossed article as the base sheet. For example, in an embossed article with a convex formed for the form of the frame layer, the dry culture layer may be formed inside the above-mentioned convex. On the other hand, an area forming the dry culture layer is concavely formed and the remaining area which is convexly formed can be used as the frame layer.

Furthermore, there is a method in which a thick hydrophobic base is used as the base sheet and a part forming the dry culture layer is concavely gouged to use the remaining part as the frame layer. Or a convex can be formed for a form of the frame layer and the dry culture layer can be formed inside this convex to use the above-mentioned convex as the frame layer. Yet, the above is not intended to impose any limitation.

(6) Lattice Print Layer

In the microorganism culture sheet of the present invention, a lattice print layer may be laminated. Such a lattice print layer may, as mentioned/described above, be formed in a base sheet or a cover sheet. In the present invention, in cases where a lamination sheet in which a paper base is laminated on a plastic sheet as the above-mentioned base sheet is used, the lattice print layer may be formed on such a paper base. For the lattice print, gravure printing or the like is preferred because a wide range of choices for coloring agents, resins, solvents, and the like is available. As for the size of the square, about 1 cm square is appropriate.

(7) Gelling Solution

The microorganism culture sheet of the present invention is required to be turned into a gel prior to culturing bacteria by administering a gelling solution to the dry culture layer.

The gelling solution can be appropriately selected corresponding to the composition of a dry culture layer composing the microorganism culture sheet. For example, in cases where the above-mentioned dry culture layer contains a gelling agent alone, the gelling solution in which nutrient components are dissolved is used. The concentration of the nutrient components is a concentration suitable to bacterial culture when a predetermined amount thereof appropriate for gelling is administered to the microorganism culture sheet. Further, a chromogenic indicator, a selective agent, substrate or the like can be included.

On the other hand, in cases where the dry culture layer contains the nutrient component, the chromogenic indicator, the selective agent, the substrate or the like, sterilized physiological saline, sterilized purified water or the like can be used as the gelling solution. As the gelling solution, a solution to be tested comprising a specific component such as the nutrient component, the chromogenic indicator, the selective agent, the substrate or the like, which component is not contained in the dry culture layer, is used, and such a specific component has a tendency to go through change in quality, change in color, degradation in a sterilization processing or other steps, such a solution is particularly beneficial. It is possible that the nutrient component alone is used as a gelling solution, whereas the chromogenic indicator, the selective agent, the substrate or the like is included in the dry culture layer.

In addition, use of the gelling solution allows to contact between the adhesive layer and the dry culture layer via the gelling solution and can thereby prevent unwanted incorporation of air bubbles.

(8) Method of Using Microorganism Culture Sheet

The microorganism culture sheet of the present invention can collect bacteria by peeling off a release film laminated on the cover sheet to expose the adhesive layer and bringing this adhesive layer into contact with a test surface. Subsequently, a predetermined amount of the above-mentioned gelling solution is administered to the dry culture layer composing microorganism culture sheet; the culture layer is covered with the above-mentioned adhesive layer after completion of gelling, the bacteria are cultured at a predetermined temperature for a predetermined period of time, microbial colonies are observed from the cover sheet or the base sheet.

For the purpose of hygiene control in a production step for food products, pharmaceutical products, or the like, using the surface of devices. facilities, or the like as a test surface, the microorganism culture sheet of the present invention is able to collect microorganisms present the above-mentioned test surface via the adhesive layer. Such a test surface is not limited to the above production step. The sheet can be preferably used for hygiene control in community facilities such as stores selling food products such as fast foods or the like, hospitals, medical offices, a lunch kitchen in schools or the like.

In addition, the microorganism culture sheet of the present invention can be used in a setting plate sampling method which is a measurement method for airborne microorganisms. The setting plate sampling method is a method of letting airborne microorganisms by themselves fall onto an uncovered agar flat plate medium with a given area for a given period of time and collecting the microorganisms. The collection is done after a given period of time, followed by culturing and measurement is carried out as the number of colonies. In an environment with a small number of the airborne microorganisms, because of that small number of the microorganisms, a longer time of the plate being uncovered is required for the detection. In cases where a conventional flat plate agar medium is used, there have been drawbacks that water evaporates and a medium becomes dry. Also, there has been a problem of drying medium in an air vent of an air conditioner or the like. However, the microorganism culture sheet of the present invention uses the dry culture layer and, after collecting bacteria, the dry culture layer is subjected to gelling or thickening using a gelling solution, which thus negates the above problems.

(9) Microorganism Culture Kit

In the present invention, the microorganism culture sheet described above and the above-mentioned gelling solution can make up a microorganism culture kit.

Using such the microorganism culture kit, grown colonies can be evaluated by peeling off the release film of the cover sheet of the above-mentioned microorganism culture sheet, bringing the adhesive layer into contact with a test surface to collect bacteria, adding the above-mentioned gelling solution and covering the dry culture layer with the adhesive layer of the cover sheet; and culturing after completion of the gelling.

Also, as a method for collecting bacteria, the release film of the cover sheet of the above-mentioned microorganism culture sheet may be peeled off and the adhesive layer may be left in a state of being uncovered for a predetermined period of time, to collect falling bacteria. Subsequently, the above-mentioned gelling solution is added and the dry culture layer is covered with the adhesive layer of the cover sheet, the dry culture layer is turned into a gel, culturing is carried out after completion of the gelling, and grown colonies can be evaluated.

When the microorganism culture kit of the present invention is used, the above microorganism culture sheet is covered with the sticking face on which bacteria are collected, and stored. And, immediately before culturing, the above gelling solution may be administered to the dry culture layer for gelling turn and the bacteria may be then cultured. In cases where there are many microorganism culture sheets on which bacteria are collected, the above operations allows work to be efficiently carried out.

The component contained in the dry culture layer used in the microorganism culture sheet and the gelling solution is closely related to culturing bacteria. Because of this, when a nutrient component, a chromogenic indicator, a selective agent, substrate or the like which is suitable to proliferation of a certain bacterium is included in the gelling solution, culture of various bacteria can be simply and conveniently carried out by combining different gelling solutions with a single microorganism culture sheet.

(10) Method of Production

When it comes to the microorganism culture sheet of the present invention, any production method may be employed as long as the dry culture layer containing at least the gelling agent can be formed on the upper side of the above-mentioned base sheet.

For example, it can be prepared by coating the base sheet with an adhesive and adhering uniformly other component such as the above gelling agent, nutrient component, a chromogenic indicator, a selective agent, substrate, buffering agent (pH adjusting agent) or the like in powder form. Any adhesive can be used as long as it does not inhibit growth of microorganisms. Preferably, an adhesive insoluble to water, for example, an acrylic-based pressure sensitive adhesive or the like can be used.

Figure 7:
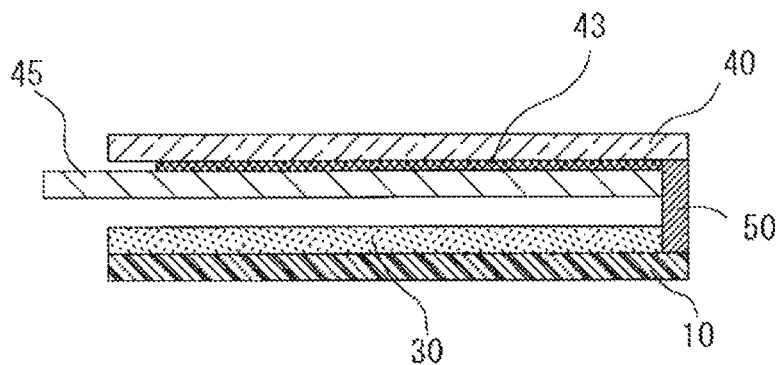

A medium solution which contains at least the gelling agent and, in addition to that, one or more from the nutrient component, a chromogenic indicator, a selective agent, substrate, buffering agent (pH adjusting agent) may be formed on the upper side of the base sheet by printing, spreading, coating, spraying, or the like. The medium solution is one in which at least a component with adhesiveness is dissolved and a component composing the dry culture layer is dissolved or dispersed, such that the component can be firmly adhered directly onto the base sheet. For example, when alcohol is used as a solvent, one in which polyvinyl pyrrolidone, hydroxy propyl cellulose, or the like is dissolved into methanol or ethanol and at least a gelling agent is dissolved, suspended, or dispersed therein can be used. When water is used as the solvent, one in which polyvinyl alcohol or polyethylene glycol or the like is dissolved into water and a gelling agent or the like is dissolved or dispersed therein can be used. The dry culture layer may be formed, as shown in the above-mentioned FIG. 1, on part of the base sheet or may be formed, as shown in FIG. 7, on the entire surface of the upper side of the base sheet.

In addition to a case where the dry culture layer is formed directly on the base sheet, the dry culture layer may be formed by fixedly setting up a nonwoven fabric on the base sheet and impregnating the above-mentioned nonwoven fabric. For example, a fabric having a mesh size of about 15 to 100 Mesh, as exemplified by synthetic fiber nonwoven fabric such as rayon nonwoven fabric or the like, natural fiber nonwoven fabric such as cotton nonwoven fabric or the like, may be placed on the base sheet and the medium solution which contains at least the gelling agent and, in addition to that, one or more from the nutrient component, a chromogenic indicator, a selective agent, substrate, buffering agent (pH adjusting agent) may be impregnated thereon by spreading, spraying or the like.

In addition, as described above, the dry culture layer may be a multiple layer with two or more layers. For example, the above-mentioned medium solution can be laminated on the base sheet and the solution containing a chromogenic indicator or the like can be then laminated thereon, thereby forming the dry culture layer providing further improved visibility of colonies.

In the present invention, it was found that use of the dry culture layer allows observation of microbial colonies and count of the number of them to the same extend where observation and count are carried out using an agar medium. On the top of that, it was found that significantly better visibility may be secured by the use of the dry culture layer, when compared with the use of an agar medium. Drying of culture layer may be required to get rid of the above-mentioned solvent contained in the medium and the drying can be carried out at temperature, pressure, or the like based on a conventionally known method.

When the microorganism culture sheet of the present invention has the frame layer on the circumference of the dry culture layer, the dry culture layer may be formed after the frame layer may be formed in advance; or the frame layer may be formed after the dry culture layer is formed. A base sheet on which the frame layer is in advance formed can be used as well.

As for the base sheet on which the frame layer is formed, there is also a method of using a base sheet having at least a hydrophobic resin on the surface thereof and the resultant is subjected to emboss processing to form the frame layer. For example, as for a base sheet on which a convex is formed for the form of the frame layer, the dry culture layer can be formed inside the above-mentioned convex to produce the microorganism culture sheet of the present invention. An area forming the dry culture layer is concavely formed by emboss processing and a convexly formed on the circumference of the above-mentioned recess can be used as the frame layer.

Meanwhile, as a method in which frame layer is formed by patterning prior to forming the dry culture layer on the base sheet, for example, a hydrophobic resin board is gouged out to a predetermined form and the resultant is adhered to the base sheet to obtain the frame layer. There is a method in which a thick a hydrophobic resin board is used as the base sheet and a part forming the dry culture layer is concavely gouged out to use the remaining part as the frame layer. Or a convex can be formed for the form of the frame layer and the dry culture layer can be formed inside this convex to use the above-mentioned convex as the frame layer.

As a hydrophobic resin, the above-mentioned UV curable ink, hot melt, heat foaming ink, UV foaming agent or the like may be used to for the frame layer by patterning. These are no solvent-based. Because patterning can be readily processed by dispenser coating or the like and curing can be readily done, they are particularly preferred.

In order for the frame layer to be formed using the above UV curable ink or the like as a hydrophobic resin, the above a hydrophobic resin may be dissolved in an appropriate solvent to carry out patterning by printing, spreading, coating, or the like.

In cases where a hydrophobic resin is an UV curable ink or an UV foaming ink, UV irradiation is applied after the patterning. With regard to conditions for the ultraviolet ray (UV) irradiation, an integral light dose is 50 to 2000 mJ/cm$^2$ and more preferably 100 to 1000 mJ/cm$^2$, and light and heat of an ultraviolet irradiation lamp can be used in combination. A range of irradiation condition to induce foaming varies depending on the type of the foaming agent. When a predetermined height is not attained at one try, the printing may repeated two or more times to form the frame layer. As the ultraviolet irradiation lamp, metal halide lamp, mercury lamp, or the like can be used.

In the present invention, in order for the frame layer to be formed after formation of the dry culture layer, the above UV curable ink, hot melt, heat foaming ink, UV foaming agent, or the like can be used to form the frame layer by patterning. In this case, when the dry culture layer contains a component whose quality is changed by UV irradiation, it is preferred that the dry culture layer be covered with a metal or the like at the time of the UV irradiation.

In addition, a hydrophobic resin board may be gouged out to a predetermined form and the resultant may be adhered to the base sheet on the circumference of the above-mentioned dry culture layer of the base sheet on which the dry culture layer is formed, thereby obtaining the frame layer.

In the microorganism culture sheet of the present invention, the adhesive layer (43) and the release film (45) are laminated on the cover sheet (40). An adhesive solution for formation of the adhesive layer on the cover sheet (40) is coated and dried to form the adhesive layer; and then the release film is laminated; and the resultant is laminated on the base sheet (10) on which the dry culture layer (30) and, as necessary, the frame layer (20) are formed. By contacting the above-mentioned adhesive layer (43) with a base sheet (10), the cover sheet (40) can be fixedly installed on the base sheet.

Meanwhile, in cases where the cover sheet and the base sheet are composed from the same component part, the adhesive layer (43) and the release film (45) may be in advance laminated on the cover sheet (40) and the resultant may be fixedly installed on the base sheet by heat sealing, laminating adhesion, or others. As shown in the plan view of FIG. 5(a) and the sectional view of FIG. 5(b), while the base sheet (10) and the cover sheet (40) are kept connected, the frame layer (20) and the dry culture layer (30) may formed on the base sheet (10). And the adhesive layer (43) and the release film (45) may be laminated on the cover sheet (40) and the resultant may folded to form the microorganism culture sheet. The sectional view is shown in FIG. 6(c). According to this method, because the base sheet (10) and the cover sheet (40) are connected, when microorganisms collected by the adhesive layer (43) is cultured on the dry culture layer (30), the adhesive layer (43) can cover the dry culture layer (30) without being out of alignment.

As shown in the transverse sectional view of FIG. 6, the cover sheet (40) on which the adhesive layer (43) and the release film (45) and the base sheet (10) may be separately prepared and then the cover sheet (40) and the base sheet (10) on which the dry culture layer (30) is formed is pasted together using a double face adhesive tape (50) or the like.

Figure 8:
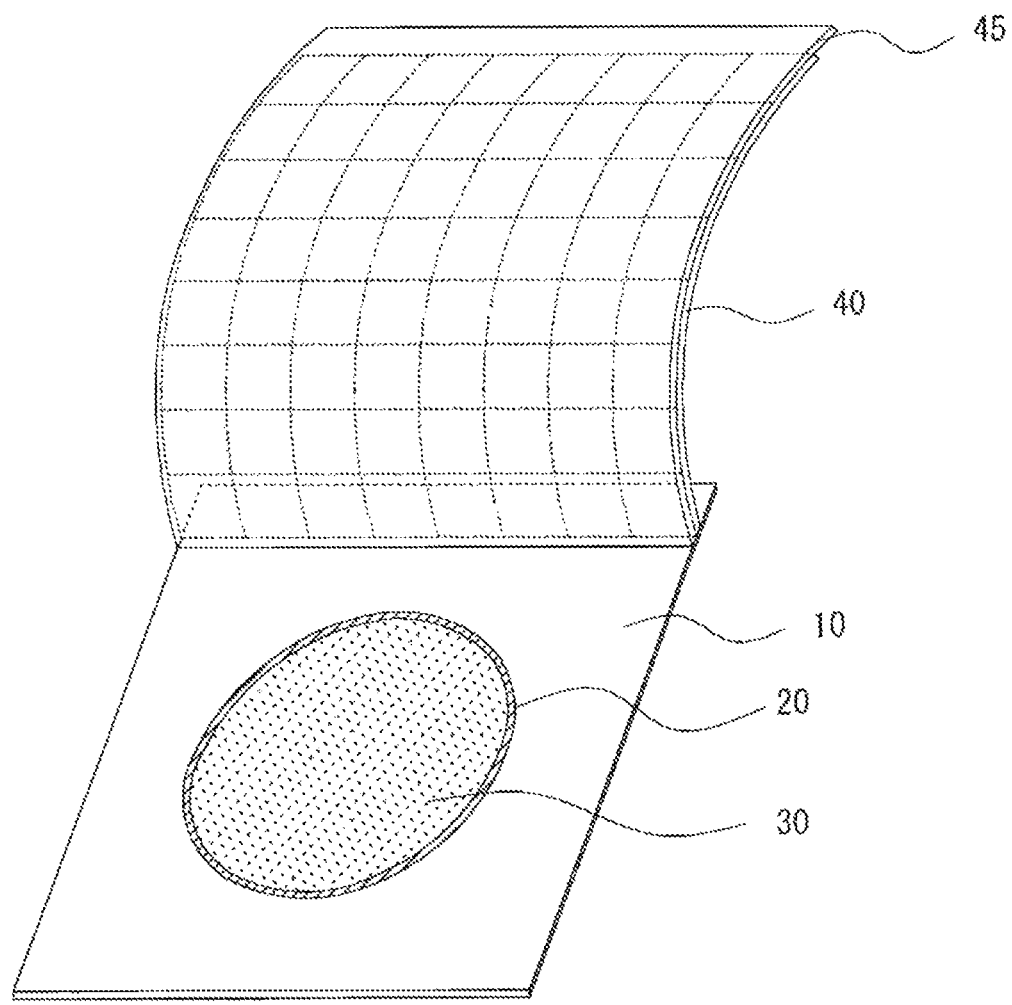

Furthermore, FIG. 8 shows an outer appearance perspective view of the microorganism culture sheet of the present invention wherein lattice print is formed on the cover sheet (40) and the cover sheet (40) and the base sheet (10) on which the dry culture layer (30) is formed are adhered at their end.

The microorganism culture sheet of the present invention is subjected to sterilization such as gamma beam irradiation, ethylene oxide gas sterilization, or the like, to obtain a product of the microorganism culture sheet of the present invention.

The microorganism culture sheet of the present invention allows carrying out culture of various microorganisms according to the type of microorganisms nutrient components contained, air permeability of the base sheet and/or the cover sheet used, or others.

EXAMPLES

By way of examples, the present invention will be concretely described below, but the present invention is by no means limited thereto.

Example 1

An UV curable ink (manufactured by Jujo Chemical Co., Ltd., trade name "Raycure GA 4100-2") was formed into a circular frame layer with a width of 1.0 mm, a height of 750 μm, and a diameter of 52 mm on a polyethylene terephthalate film (manufactured by Teijin DuPont Films Japan Limited, trade name "Teijin Tetoron film") using a dispenser. The frame layer was cured with an integral light dose of 250 mJ/cm$^2$ using a mercury lamp. The obtained frame layer had a height of 750 μm (difference from the height of a dry culture layer: +400 μm) and a width of 1 mm.

Then, 20 g of polyvinyl pyrrolidone K-90 was dissolved in 210 ml of methanol. To the resultant, 60 g of guar gum powder (manufactured by Sansho Co., Ltd., trade name "NEOVISCO G", 400 mesh type) was dispersed. Further, as nutrient components, 3.26 g of tryptone (manufactured by Becton, Dickinson and Company, trade name "BACT TRYPTONE"), 0.82 g of meat extract (manufactured by Oxoid Limited, trade name "Lab-Lemco"), 0.03 g of yeast extract (manufactured by Becton, Dickinson and Company, trade name "YEAST EXTRACT"), 0.16 g of glucose (manufactured by Wako Pure Chemical Industries, Ltd., trade name "D-(+)-GLUCOSE"), 0.41 g of sodium chloride (manufactured by Wako Pure Chemical Industries, Ltd.), 0.37 g of disodium hydrogen phosphate (manufactured by Wako Pure Chemical Industries, Ltd.) were mixed to adjust a coating solution.

This solution containing the nutrient components and the gelling agent was, using the dispenser, spread into the frame of the base on which the above-mentioned frame layer was formed. The layer spread was then dried at 50° C. for 15 minutes to form a dry culture layer. When dried, the layer had a thickness of 350 μm.

Subsequently, 1 part by weight of an isocyanate-based curing agent (L-45/Soken Chemical & Engineering Co., Ltd.) was mixed in 100 parts by weight of an acrylic-based adhesive (SK Dyne 1495/Soken Chemical & Engineering Co., Ltd.); and the resultant was spread on a siliconized polyester film having a thickness of 50 μm so as to attain a thickness after drying of 20 nm, which was pasted together with a side with corona treatment of an OPP film with a thickness of 40 μm (OP-U-1/Tohcello Co., Ltd.) to produce an adhesive layer. The layer was formed on a PET base on which the above-mentioned frame layer and the dry culture layer were formed and their ends were adhered. The thus obtained article was sterilized using gamma rays, thereby obtaining a microorganism culture sheet of the present invention.

As a bacterial strain, *Staphylococcus aureus* (*Staphylococcus aureus* ATCC25923) was used. A bacterial liquid obtained by culturing the bacteria in a liquid medium (TRYPTIC SOY BROTH) at 36±1° C. for 18 hours was diluted with sterilized physiological saline such that the number of the bacteria was 10$^3$/ml. One mL of the resultant was dropped on the surface of a rubber board and air-dried. This surface was used as an object to be tested. On the obtained rubber board with an area of 200 cm$^2$, 1×10$^3$ of *Staphylococcus aureus* were attached. A release film comprising a polyester film of the above microorganism culture sheet was peeled off and the adhesive layer was put once onto the object to be tested, namely the above-prepared rubber board, by applying pressure, thereby collecting *Staphylococcus aureus*.

Subsequently, using a sterilized pipette, 1 ml of sterilized purified water which was added with TTC at 0.05 g/L was added onto the dry culture layer of the above microorganism culture sheet, which was covered with the cover sheet. The above-mentioned sterilized purified water was spread all over the entire frame layer. The sheet was left to stand for about one minute to allow gel formation and placed in an incubator, incubated at 36±1° C. for 48 hours.

Figure 9:
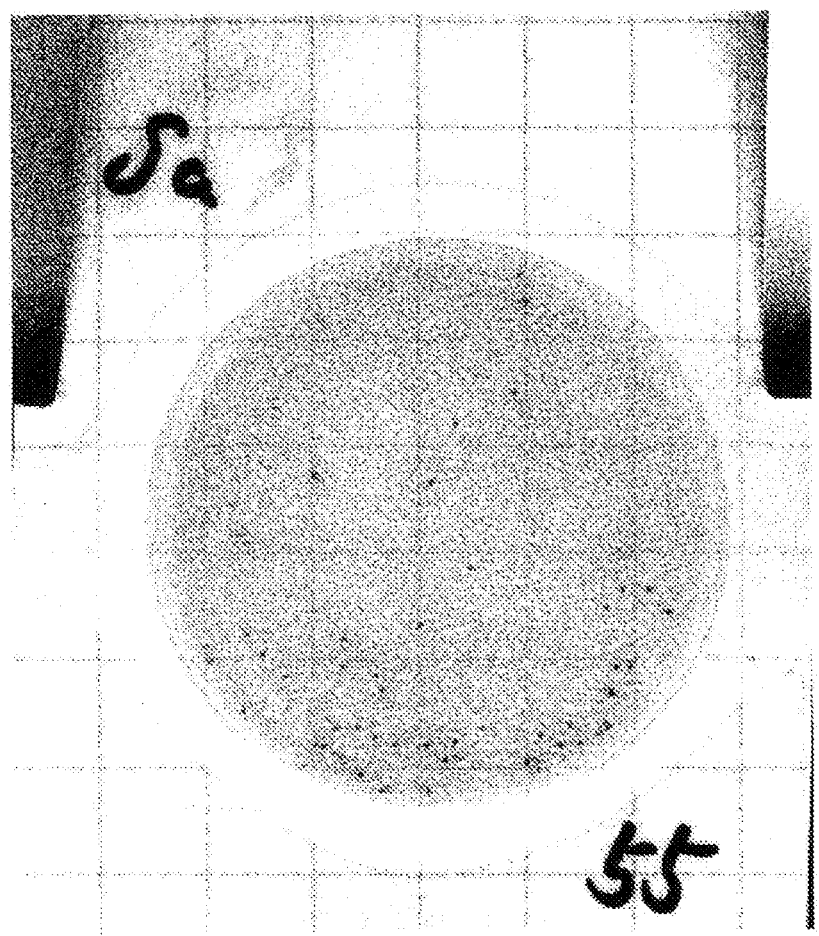

After incubation, the number of colonies grown was individually counted. The results are shown in Table 1. Also, the grown colonies are shown in FIG. 9.

Comparative Example 1

A commercially available sheet for microorganism detection (manufactured by Chisso Corporation, trade name "Sanita-kun", for general viable bacteria) was used. The cover of this sheet for microorganism detection was opened and 1 ml of sterilized physiological saline was added to a nonwoven fabric part. The sheet was left to stand for 15 minutes. A release film of the above sheet for microorganism detection was peeled off and the nonwoven fabric part was put once onto the object to be tested which was prepared in the same way as in Example 1 with applying pressure, thereby collecting *Staphylococcus aureus*.

Subsequently, a moistened nonwoven fabric of the above sheet for microorganism detection was covered with the cover sheet and the sheet was placed in an incubator and incubated at 36±1° C. for 48 hours. After incubation, the number of colonies grown was individually counted. The results are shown in Table 1.

Example 2

A cover sheet of a sheet for detection of Comparative Example 1 was peeled off. A cover sheet of Example 1 was used and an object to be tested prepared in the same way as in Example 1 was used. A release film of the above sheet for microorganism detection was peeled off and an adhesive layer was put once onto the object to be tested by applying pressure, thereby collecting *Staphylococcus aureus*.

Subsequently, 1 ml of sterilized physiological saline was added to a nonwoven fabric part of the sheet for microorganism detection used in Comparative Example 1. The nonwoven fabric part was adequately moistened and then covered with the adhesive layer of the cover sheet. The sheet was placed in an incubator and incubated at 36±1° C. for 48 hours. After incubation, the number of colonies grown was individually counted. The results are shown in Table 1.

Comparative Example 2

For a medium, 2.5 g of yeast extract (manufactured by Becton, Dickinson and Company), 5.0 g of tryptone (Becton, manufactured by Dickinson and Company, trade name "BACT TRYPTONE"), 1.0 g of (D-(+)-glucose (manufactured by Nacalai Tesque, Inc.), and 15.0 g of agar were added in 1000 mL of purified water to obtain a uniform suspension. The suspension was autoclaved at 121° C. for 15 minutes and allowed to cool to 50° C., which was aliquoted into vessels to obtain a standard agar nutrient medium. Using this, a stamp medium with a thickness of 3.5 mm and an area of 10 cm$^2$ was prepared. This medium was sterilized using gamma rays, thereby obtaining a comparative stamp medium.

The above comparative stamp medium was put once onto the object to be tested which was prepared in the same way as in Example 1 by applying pressure, thereby collecting *Staphylococcus aureus*.

Figure 10:
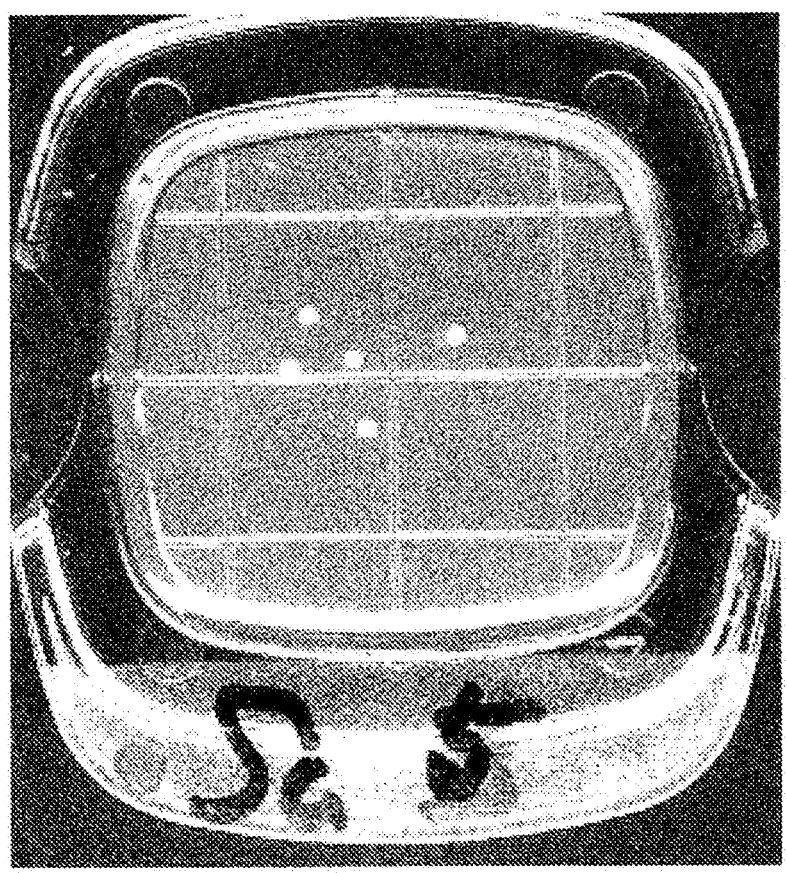

A lid was then placed over the above comparative stamp medium, which was placed in an incubator and incubated at 36±1° C. for 48 hours. After incubation, the number of colonies grown was individually counted. The results are shown in Table 1. Also, the grown colonies are shown in FIG. 10.

TABLE 1

Results of colony measurement (unit: colonies)

|  | Number of Colonies |
|---|---|
| Example 1 | 55 |
| Comparative Example 1 | 4 |
| Example 2 | 33 |
| Comparative Example 2 | 5 |

(Results)

In Comparative Example 1 and Comparative Example 2, the hydrous culture layer was brought into direct contact with the test object to collect microorganisms. The number of the cultured colonies was 4 and 5, respectively. In contrast to this, in Example 1 and Example 2, the adhesive layer uncovered by peeling the release film was brought into direct contact with the test object to collect microorganisms. The number of the colonies was 55 and 33. From this, it was found that a method in which the adhesive layer uncovered by peeling the release film was brought into direct contact with the test object to collect microorganisms was excellent in collection efficiency.

In addition, when colonies in Example 1 shown in FIG. 9 was compared with colonies in Comparative Example 2 shown in FIG. 10, it was found that use of the dry culture layer in Example 1 provided more excellent visibility of the colonies than use of the agar medium in Comparative Example 2.

Example 3

As the above-mentioned dry culture layer, (i) a microorganism culture sheet prepared with the same composition as Example 1 and (ii) a microorganism culture sheet prepared by the same operations as Example 1 except that the dry culture layer does not contain nutrient components were used. The release film of the above sheet for microorganism detection was peeled off and the adhesive layer was put once against a test object by applying pressure, thereby collecting *Staphylococcus aureus*. In the above (i) and (ii), the thickness of the dry culture layer was, when dried, 320 to 360 μm.

Subsequently, when the microorganism culture sheet of (i) was used, 1 ml of a predetermined dilution solution (gelling solution) was added onto the dry culture layer of the above-mentioned microorganism culture sheet. When microorganism culture sheet of (ii) was used, 1 ml of a nutrient component solution (gelling solution) obtained by dissolving 20.0 g of tryptone (manufactured by Becton, Dickinson and Company, trade name "BACT TRYPTONE"), 5.0 g of meat extract (manufactured by Oxoid Limited, trade name "Lab-Lemco"), 1.0 g of yeast extract (manufactured by Becton, Dickinson and Company, trade name "YEAST EXTRACT"), 1.0 g of glucose (manufactured by Wako Pure Chemical Industries, Ltd., trade name "D-(+)-GLUCOSE"), 1.0 g of sodium chloride (manufactured by Wako Pure Chemical Industries, Ltd.), 1.0 g of disodium hydrogen phosphate (manufactured by Wako Pure Chemical Industries, Ltd.), 0.05 g of TTC (manufactured by Wako Pure Chemical Industries, Ltd.) into 1000 ml of sterilized purified water was added onto the dry culture layer of the above-mentioned microorganism culture sheet. Each of the layers was covered with the cover sheet. The above-mentioned gelling solution was spread in the entire frame layer. The sheet was left to stand for about one minute to allow gel formation, placed in an incubator and incubated at 36±1° C. for 48 hours. After incubation, the number of colonies grown was individually counted. The results are shown in Table 2.

TABLE 2

Results of colony measurement (unit: colonies)

| Dry culture layer | Number of colonies |
|---|---|
| With nutrient components | 171 |
| Without nutrient components | 195 |

(Results)

The number of the colonies detected when the dry culture layer contained the nutrient component and was turned into a gel using the gelling solution without the nutrient component was substantially comparable to that when the dry culture layer did not contain the nutrient component and was turned into a gel using the gelling solution with the nutrient component. From this, it was found that use of the gelling solution with the nutrient component for turning the dry culture layer into a gel allows detection of varied bacteria by adding different gelling solutions at the time of production of microorganism culture sheet, which may enable production lines to be unified.

Example 4

The release film (polyester film) of the adhesive layer of the microorganism culture sheet produced in Example 1 was peeled off and a finger was pressed into the sticking face. A sterilized purified water which was added with TTC at 0.05 g/L was then aliquoted to the dry culture layer of the above-mentioned microorganism culture sheet. Subsequently, while the culture layer is being covered with the sticking face of the above-mentioned adhesive layer, the above-mentioned sterilized purified water was spread all over the frame layer of the microorganism culture sheet. The sheet was left to stand for one minute to allow gel formation, then placed in an incubator, and incubated at 36±1° C. for 48 hours. The number of the grown colonies after incubation is shown in FIG. 11.

Comparative Example 3

A commercially available stamp medium DD checker (manufactured by Kyokuto Pharmaceutical Industrial Co., Ltd., DD agar medium for detection of general bacteria) was used. A finger was pressed into the surface of an agar medium in the left side and one obtained by pressing a finger to the adhesive layer of microorganism culture sheet in the same way as Example 4 was pasted to an agar medium in the right side. This was placed in an incubator and incubated at 36±1° C. for 48 hours. The number of the grown colonies after incubation is shown in FIG. 12.
(Results)

Figure 11:
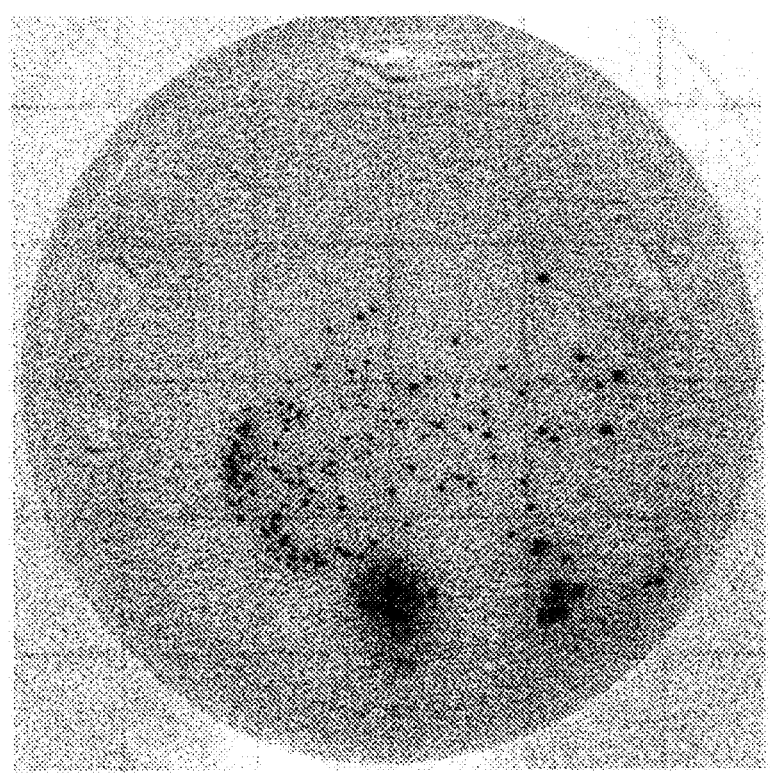

As shown in FIG. 11, combination of the microorganism culture sheet comprising dry culture layer with the adhesive layer of the cover sheet gave very high visibility and allowed good distinction of colonies.

In contrast, as shown in the right side of FIG. 12, when the adhesive layer was combined with the agar medium, fine air bubbles or the like are easily incorporated and colonies diffused between the adhesive layer and the agar, which created no contrast. The colonies were thus hard to be seen.

The microorganism culture sheet of the present invention is able to provide a microorganism culture sheet with an excellent collection efficiency of microorganisms. The dry culture layer gives superior visibility of colonies to an agar medium and is thus useful.

REFERENCE SIGNS LIST

10 Base sheet
20 Frame layer
30 Dry culture layer
40 Cover sheet
43 Adhesive layer
45 Release film
50 Double face adhesive tape

The invention claimed is:

1. A microorganism culture sheet consisting of a base sheet, a dry culture layer formed on said base sheet, a frame layer, and a cover sheet directly covering said dry culture layer, wherein:
    said dry culture layer is formed in a circle shape by patterning a medium suspension consisting of a gelling agent dispersed in an alcohol, polyvinyl pyrrolidone dissolved in the alcohol, and nutrients for culturing microorganisms on said base sheet and then drying to remove the alcohol, said dry culture layer has a circumference and a height, and said gelling agent is selected from the group consisting of carrageenan, guar gum, xanthan gum, locust bean gum, and algin;
    the dry culture layer is present on the base sheet in an amount of 5 to 400 g/m$^2$;
    said frame layer is formed in a hydrophobic resin on said base sheet around said dry culture layer; and
    said cover sheet has an inner surface, an adhesive layer on the inner surface, and a release film laminated on the adhesive layer so that upon removal of the release film, the adhesive layer is capable of collecting a bacterium.

2. The microorganism culture sheet according to claim 1, wherein said adhesive layer has a thickness of 1 to 100 µm.

3. The microorganism culture sheet according to claim 1, wherein said frame layer is higher than the height of said dry culture layer by 100 to 1200 µm.

4. The microorganism culture sheet according to claim 1, wherein said base sheet and/or cover sheet are/is made of a transparent plastic sheet.

5. The microorganism culture sheet of claim 1 wherein the dry culture layer contains substantially no water.

6. The microorganism culture sheet of claim 1, wherein said alcohol is at least one selected from the group consisting of methanol and ethanol.

7. A microorganism culture kit comprising said microorganism culture sheet according to claim 1 and a gelling solution.

8. A microorganism culture sheet consisting of a base sheet, a dry culture layer formed on said base sheet, a frame layer, and a cover sheet directly covering said dry culture layer, wherein:
    said dry culture layer is formed in a circle shape by patterning a medium suspension consisting of a gelling agent dispersed in an alcohol, polyvinyl pyrrolidone dissolved in the alcohol, nutrients for culturing microorganisms, and at least one other component selected from the group consisting of chromogenic indicator, selective agent, substrate, and buffering agent, on said base sheet and then drying to remove the alcohol, said dry culture layer has a circumference and a height, and said gelling agent is selected from the group consisting of carrageenan, guar gum, xanthan gum, locust bean gum, and algin;
    the dry culture layer is present on the base sheet in an amount of 5 to 400 g/m$^2$;
    said frame layer is formed in a hydrophobic resin on said base sheet around said dry culture layer; and
    said cover sheet has an inner surface, an adhesive layer on the inner surface, and a release film laminated on the adhesive layer so that upon removal of the release film, the adhesive layer is capable of collecting a bacterium.

9. A method for culturing a bacterium collected on said adhesive layer of said microorganism culture sheet in said microorganism culture kit according to claim 7, wherein said method comprising the steps of collecting said bacterium in said adhesive layer, turning said dry culture layer of said microorganism culture sheet into a gel by adding said gelling solution and covering with said adhesive layer of said cover sheet, and culturing after the completion of gelling.

10. The method for culturing a bacterium according to claim 9, comprising bringing said adhesive layer into contact with a test surface to collect said bacterium.

11. The method for culturing a bacterium according to claim 9, comprising leaving said adhesive layer uncovered for a prescribed time to collect falling bacterium.

* * * * *